US009670257B2

(12) United States Patent
Shaw et al.

(10) Patent No.: US 9,670,257 B2
(45) Date of Patent: Jun. 6, 2017

(54) METHODS FOR PRODUCING PEPTIDES USING ENGINEERED INTEINS

(71) Applicant: Novo Nordisk A/S, Bagsvaerd (DK)

(72) Inventors: Allan Christian Shaw, Copenhagen N (DK); Jens Christian Norrild, Birkeroed (DK); Louise Albertsen, Copenhagen OE (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/893,349

(22) PCT Filed: May 28, 2014

(86) PCT No.: PCT/EP2014/061048
§ 371 (c)(1),
(2) Date: Nov. 23, 2015

(87) PCT Pub. No.: WO2014/191455
PCT Pub. Date: Dec. 4, 2014

(65) Prior Publication Data
US 2016/0096872 A1    Apr. 7, 2016

Related U.S. Application Data

(60) Provisional application No. 61/833,046, filed on Jun. 10, 2013.

(30) Foreign Application Priority Data

May 31, 2013  (EP) .................................... 13170009

(51) Int. Cl.
C07K 14/47     (2006.01)
C07K 14/575    (2006.01)
C07K 1/00      (2006.01)
C12N 15/62     (2006.01)
C12N 9/90      (2006.01)
C07K 7/00      (2006.01)
C12N 15/09     (2006.01)

(52) U.S. Cl.
CPC .............. *C07K 14/47* (2013.01); *C07K 1/006* (2013.01); *C07K 7/00* (2013.01); *C07K 14/575* (2013.01); *C12N 9/90* (2013.01); *C12N 15/09* (2013.01); *C12N 15/625* (2013.01); *C07K 2319/00* (2013.01); *C07K 2319/92* (2013.01)

(58) Field of Classification Search
None
See application file for complete search history.

(56) References Cited

FOREIGN PATENT DOCUMENTS

| EP | 1117693 A2 | 7/2001 |
|---|---|---|
| WO | 98/50563 A1 | 11/1998 |
| WO | 00/00625 | 1/2000 |
| WO | 2004/029245 A1 | 4/2004 |
| WO | 2012036962 A2 | 3/2012 |
| WO | 2012/100176 A2 | 7/2012 |
| WO | 2013/045632 A1 | 4/2013 |

OTHER PUBLICATIONS

Cottingham et al. "A method for the amidation of recombinant peptides expressed as intein fusion proteins in *Escherichia coli*," Nature Biotechnology 19, 974-977 (2001).*
Albertsen et al. "Recombinant Production of Peptide C-Terminal [alpha]-Amides Using an Engineered Intein" Bioconjugate Chemistry. 2013. pp. 1883-1894.
Bjorklund M et al "Use of intein-directed biosynthesis to improve serum stability and bioactivity of a gelatinase inhibitory peptide" Combinatorial Chemistry and High Throughput Screening. 2003 vol. 6 pp. 29-35.
Chen et al. "Expression of a cytotoxic cationic antibacterial peptide in *Escherichia col* i using two fusion partners" Protein Expression and Purification. 2008 vol. 57(2) pp. 303-311.
Cottingham et al. "A method for the amidation of recombinant peptides expressed as intein fusion proteins in *Escherichia coli*" Nature Biotechnology. vol. 19:10 pp. 974-977.
Cui et al. "Elimination of in vivo cleavage between target protein and intein in the intein-mediated protein purification systems" Protein Expression and Purification. vol. 5:1 pp. 74-81.
Gerrit Volkmann et al "Protein C-Terminal Labeling and Biotinylation Using Synthetic Peptide and Split-Intein" PLOS One 2009, vol. 4(12) p. e8381.
Hiraga et al. "Minimization and stabilization of the *Mycobacterium tuberculosis* recA intein" Journal of Molecular Biology. 2005. vol. 354(4) pp. 916-926.

(Continued)

*Primary Examiner* — Christina Bradley
(74) *Attorney, Agent, or Firm* — Rosemarie R. Wilk-Orescan

(57) ABSTRACT

The present invention provides a method for producing peptides by recombinant means. The peptides are expressed as part of a fusion protein comprising the target peptide and an engineered intein. The invention also provides the engineered inteins, fusion proteins comprising these, and DNA constructs coding for these fusion proteins. Upon thiol-induced cleavage of the fusion protein the carboxy-terminal α-thioester of the target peptide is obtained. The carboxy-terminal α-thioester can in principle react with any nucleophile and the strategy therefore allows a wider range of carboxy-terminal modifications such as chemical ligation, bioconjugation, or amidation. The engineered inteins of the present invention are minimized in size and has a cysteine mutation in the position corresponding by alignment to position 3 of Mxe GyrA intein (SEQ ID NO:1) leading to increased expression levels of the fusion protein and higher yields of the isolated target peptide, thus making the method of the invention suitable for production scale.

15 Claims, 2 Drawing Sheets

(56) References Cited

OTHER PUBLICATIONS

P. L. Starokadomskyy et al "Utilization of protein splicing for purification of the human growth hormone" Applied Molecular Biology. 2008 vol. 42(6) pp. 966-972.
Sharma et al. "Intein-mediated protein purification of fusion proteins expressed under high-cell density conditions in *E. coli*" Journal of Biotechnology. 2006 vol. 125(1) pp. 48-56.
Telenti et al. "The *Mycobacterium xenopi* GyrA protein splicing element: characterization of a minimal intein" Journal of Bacteriology. 1997 vol. 179(20) pp. 6378-6382.

\* cited by examiner

METHODS FOR PRODUCING PEPTIDES USING ENGINEERED INTEINS

CROSS-REFERENCE TO RELATED APPLICATIONS

This application is a 35 U.S.C. §371 National Stage application of International Application PCT/EP2014/061048 (published as WO 2014/191455), filed May 28, 2014, which claimed priority of European Patent Application 13170009.8, filed May 31, 2013; this application claims priority under 35 U.S.C. §119 of U.S. Provisional Application 61/833,046, filed Jun. 10, 2013, the contents thereof which are incorporated by reference in their entirety.

TECHNICAL FIELD

The present invention relates to methods of producing peptides comprising expression of the peptide as part of a fusion protein, wherein said fusion protein comprises a target peptide and an engineered intein.

SEQUENCE LISTING

The instant application contains a Sequence Listing which has been submitted in ASCII format via EFS-Web and is hereby incorporated by reference in its entirety. Said ASCII copy, created on Nov. 19, 2015 is the same as the Sequence Listing filed in International Application No. PCT/EP2014/061048, is named 8672US02_SeqList.txt and is 31 kilobytes in size.

BACKGROUND

Peptides are a rapidly growing class of therapeutics with more than 50 peptide-based products currently on the market and even more in development covering disease areas such as immunology, oncology, neurology and endocrinology. Peptides regulate a plethora of physiological functions, mainly by interactions with specific cellular receptors, whereby they induce cellular signalling events, such as neurotransmission and release of hormones. Endogenous peptides have been associated with challenges as therapeutics due to their limited in vivo stability and bioavailability. However, the high specificity and low toxicity combined with improved ability to selectively modify and improve therapeutic properties of peptides has increased the relevance of peptides in drug development.

In endocrinology, diseases are often caused by or associated with an imbalance of the level of peptide hormones, as seen in diseases such as diabetes and obesity. Notably, about half the peptide hormones in the endocrine and nervous systems are α-amidated in their C-terminal and the α-amide moiety is often crucial for biological activity and stability. Certain therapeutic peptides including peptide hormones involved in obesity and diabetes (e.g. peptide YY (PYY), pancreatic peptide (PP), α-calcitonin gene related peptide (α-CGRP), calcitonin (CT), and amylin) require an α-amide moiety in the C-terminal to obtain full biological activity.

The most widely used technologies for production of peptide therapeutics are microbial expression systems and chemical synthesis. While a peptide C-terminal amide is easily achieved by chemical synthesis, it is not readily introduced into recombinant peptides derived from microbial hosts, which lack an α-amidating enzymatic machinery. Therefore, the α-amide has to be introduced as a post translational modification.

Inteins are autocatalytic protein domains which are expressed in unicellular organisms with flanking protein sequences at both amino- and carboxy-termini. The amino- and carboxy-terminal sequences have been named exteins in keeping with the DNA nomenclature of exons and introns. A seemingly typical member of the emerging family of inteins is the GyrA gene product from *Mycobacterium xenopi* (Mxe GyrA). This is approximately 22 kDa in molecular mass and contains a number of crucial amino acids at the amino-terminus (cysteine) and at the carboxy-terminus (histidine and asparagine). In addition, the carboxy-terminal extein must start with a cysteine, serine or threonine. At some point after translation is completed, the peptide bond between the amino-terminal extein and the intein is converted into a thioester bond by an N-to-S acyl shift involving the cysteine at the amino-terminal of the intein. This bond is then exchanged with the nucleophilic residue (serine, threonine or cysteine) at the start of the carboxy-terminal extein and then, with participation of the asparagine at the C-terminus of the intein, the intein excises itself out, while a second acyl shift generates a native peptide bond between the amino- and carboxy-terminal exteins. The overall effect of these concerted reactions is that the two exteins are seamlessly joined and the intein is released.

Mutant inteins have been designed where the self-splicing function has been disabled by a mutation to allow cleavage at either the amino- or carboxy-terminal splice junctions. For the Mxe GyrA intein, amino-terminal cleavage has been enabled by a N198A mutation. Replacement of the amino-terminal extein by another polypeptide sequence, the target peptide, enables preparation of the target peptide with a reactive carboxy-terminal α-thioester handle after cleavage of the resulting fusion protein with a nucleophilic chemical agent such as sodium 2-mercaptoethanesulfonate (MESNa). Such intein-derived α-thioesters can be reacted with any nucleophile and is useful as a chemical handle for chemical ligation, bioconjugation or amidation. The intein-based approach has been used to generate α-amidated peptides recombinantly in a laboratory scale (WO 98/50563 A1; WO 00/00625 A1; Cottingham I. R. et al., Nat. Biotechnol. 2001, 19, 974-977).

The primary limitation of using this technology for large scale production of C-terminally α-amidated peptides is the low yields generally observed, which may be ascribed to a combination of the large size of the intein and hydrolytic instability of the intein fusion protein. Introduction of a T3C mutation in the Mxe GyrA intein has been shown to be associated with reduced premature cleavage (Cui C. et al. *Protein Expr. Purif.* 2006, 50, 74-81). Furthermore, the size of the intein is large relative to that of the peptide hormones and a reduction in intein size could potentially improve the final yield of the peptide hormone by a more economical usage of the host protein synthesis machinery.

SUMMARY

The present invention provides a method for producing peptides by recombinant means. The peptides are expressed as part of a fusion protein comprising the target peptide and an engineered intein and upon thiol-induced cleavage of the fusion protein the carboxy-terminal α-thioester of the target peptide is obtained. The carboxy-terminal α-thioester can in principle react with any nucleophile and the strategy therefore allows a wider range of carboxy-terminal modifications such as chemical ligation, bioconjugation, or amidation. Another advantage of the intein-based strategy is that the peptide α-thioester is generated by thiolysis of the peptide-intein fusion protein, potentially avoiding the need for processing enzymes.

In one aspect, the invention provides a method for producing a peptide, which comprises the step of expressing the peptide as part of a fusion protein, wherein said fusion protein comprises a target peptide and an intein, wherein said intein is minimized in size and carries a cysteine mutation in the position corresponding by alignment to position 3 of Mxe GyrA intein (SEQ ID NO:1).

In another aspect, the invention provides a fusion protein comprising a target peptide and an intein, wherein said intein is minimized in size and carries a cysteine mutation in the position corresponding by alignment to position 3 of Mxe GyrA intein (SEQ ID NO:1). In another aspect, the invention provides an intein which is minimized in size and carries a cysteine mutation in the position corresponding by alignment to position 3 of Mxe GyrA intein (SEQ ID NO:1).

In another aspect, the invention provides a DNA construct encoding a fusion protein comprising at least a target peptide and an intein, wherein said intein is minimized in size and carries a cysteine mutation in the position corresponding by alignment to position 3 of Mxe GyrA intein (SEQ ID NO:1).

The recombinant production of peptide α-thioesters using an intein-based approach involving expression of the target peptide as an amino-terminal fusion to the intein has been limited to laboratory scale due to low yields of target peptides.

The engineered inteins of the present invention are minimized in size and has a cysteine mutation in the position corresponding by alignment to position 3 of Mxe GyrA intein (SEQ ID NO:1) leading to increased expression levels of the fusion protein and higher yields of the isolated target peptide, thus making the method of the invention suitable for production scale.

DESCRIPTION

Figure 1:
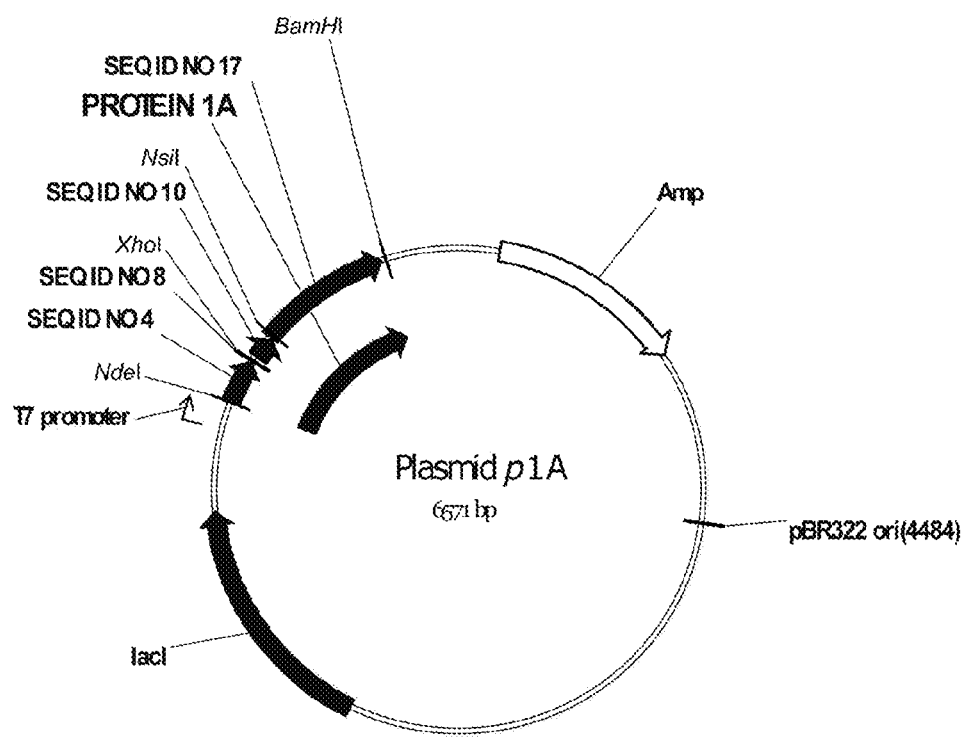
FIG. 1: Representative pET11a vector map of plasmid 1A encoding [Gly4]-hPYY4-36 (SEQ ID NO: 10) fused between an amino-terminal tag (SEQ ID NO: 4) containing a protease site (SEQ ID NO: 8) and a carboxy-terminal GyrA intein variant (SEQ ID NO: 17). The entire fusion protein is marked with the feature Protein 1A. NdeI, NheI, NsiI, XhoI and BamHI restriction enzyme sites are depicted. T7 promoter region, Ampecillin resistance gene, lacI repressor region and origin of replication site are also shown in the vector map.

Peptides are of increasing interest as therapeutics in a wide range of diseases, including metabolic diseases such as diabetes and obesity. Certain therapeutic peptides including peptide hormones involved in obesity and diabetes (e.g. PYY, PP, α-CGRP, CT, and amylin) require an α-amide moiety in the carboxy-terminal to obtain full biological activity. A challenge is to generate such peptides by recombinant means and particularly in a production scale.

The invention provides engineered inteins, which has been minimized in size and carries a cysteine point mutation in the position corresponding by alignment to position 3 of Mxe GyrA intein (SEQ ID NO:1). The inteins can be used for recombinant production of peptides, where the peptides are expressed as part of a fusion protein comprising the target peptide and an engineered intein of the invention (see FIG. 2). The combination of the cysteine mutation in the position corresponding by alignment to position 3 of Mxe GyrA intein (SEQ ID NO:1) and the minimization of the intein increase the expression yield of intein fusion proteins and hence the yield of the target peptide. The latter is obtained by thiol-induced cleavage of the fusion protein leading to the α-thioester of the target peptide, which can be converted to the corresponding α-amide of the target peptide by addition of an ammonia nucleophile such as ammonia bicarbonate. The engineered inteins of the invention thus provide an optimised strategy for production of α-amidated peptide hormones such as PYY, PP, amylin, and α-CGRP. Due to the higher expression yields and higher yields of the isolated target peptides, the invention thus provides a method for recombinant production of α-amidated peptides in production scale.

The α-thioester generated by this method can also be used for chemical ligation or bioconjugations, and in one aspect, the invention provides a method for recombinant production of carboxy-terminal bioconjugated proteins and peptides.

In one aspect, the present invention relates to a method for producing a peptide, which comprises the step of expressing the peptide as part of a fusion protein, wherein said fusion protein comprises a target peptide and an intein, wherein said intein is minimized in size and has a cysteine mutation in the position corresponding by alignment to position 3 of Mxe GyrA intein (SEQ ID NO:1).

In one aspect, the invention provides a fusion protein comprising a target peptide and an intein, wherein said intein is minimized in size and carries a cysteine mutation in the position corresponding by alignment to position 3 of Mxe GyrA intein (SEQ ID NO:1). In one aspect, the invention provides an intein which is minimized in size and carries a cysteine mutation in the position corresponding by alignment to position 3 of Mxe GyrA intein (SEQ ID NO:1). In one aspect, the invention provides a DNA construct encoding a fusion protein comprising a target peptide and an intein, wherein said intein is minimized in size and carries a cysteine mutation in the position corresponding by alignment to position 3 of Mxe GyrA intein (SEQ ID NO:1).

Inteins are autocatalytic protein domains which are expressed in unicellular organisms with flanking protein sequences at both amino- and carboxy-termini. In one aspect, the intein is a GyrA intein. The GyrA inteins are a class of inteins that are inserted within the gene sequence coding for DNA gyrase subunit A of some bacteria, typically *Mycobacterium* species. This class of inteins consist of 16 different inteins that share high sequence homology and are characterized by having a Cys in the amino-terminal and His-Asn in the carboxy-terminal. Moreover, all of these inteins are recognized by having a Tyr in the carboxy-terminus of the amino-terminal-extein and a Thr in the amino-terminus of the carboxy-terminal-extein. Generally, these inteins have a size of approximately 420 amino acids and the amino- and carboxy-terminal splicing regions are interrupted by a DOD homing endonuclease domain. However, the Mxe GyrA intein lacks a DOD homing endonuclease domain and has compared to other GyrA inteins a smaller amount of residues between the amino- and carboxy splicing domains, resulting in an overall size of 198 amino acids. An X-ray crystal structure of this intein has shown that this region, which corresponds to amino acid residues 107-164, consist of two α-helices as well as an unstructured region that projects out from and is not part of the characteristic HINT splicing domains of inteins.

In one aspect, the intein is the Mxe GyrA intein, which has been extensively used at a laboratory scale to generate protein α-thioesters for chemical ligation purposes. This intein possesses several advantageous properties such as the ability to be refolded from bacterial inclusion bodies, retains activity in the presence of denaturants and low sequence requirements to the carboxy-terminal residue of the amino terminal-extein. The amino acid sequence of Mxe GyrA intein is shown in SEQ ID NO: 1.

In one aspect, the intein is a Mxe GyrA intein minimized in size by excision of a part of the residues 107-164 or replacement of the excised residues with a linker of sequence GSGSGSGS.

In one aspect, the intein is a Mxe GyrA intein minimized in size by excision of residues 107-160 and replacement of the excised residues with a linker of sequence GSGSGSGS. In one aspect, the intein is a minimised Mxe GyrA intein carrying a T3C mutation with the sequence of SEQ ID NO: 20.

In one aspect, the target peptide is a peptide hormone that is α-amidated in its carboxy-terminal. Around 50% of all mammalian peptide hormones are α-amidated in their carboxy-terminal and this α-amide functionality is often crucial for the biological activity. Several peptide hormones are today used as drugs in the treatment of metabolic diseases such as diabetes and/or obesity. An example is amylin (e.g. Symlin®, pramlintide acetate, an analogue of human amylin). Human amylin is a 37 residues α-amidated peptide hormone that can be used to treat or prevent diabetes and/or obesity. Accordingly, the carboxy-terminal of amylin needs to be α-amidated to obtain full biological activity. Likewise PYY, PP, CT and α-CGRP should be α-amidated to obtain full biological activity. The carboxy-terminal α-amide moiety may also serve as protection against proteolytic degradation. A comparison of carboxy-terminal α-amidated and non-amidated glucagon-like peptide-1 (GLP-1) indicates that the amidation does not affect overall biological effects observed on insulin and glucagon secretion. However, extensive carboxy-terminal degradation occurs in plasma for the non-amidated variant. Thus, for some peptide and proteins carboxy-terminal amidation may be beneficial to introduce as a mean of prolonging the presence of the full-length and biologically active protein in plasma. The present invention therefore provides an alternative method for obtaining peptides or proteins, which are carboxy-terminal α-amidated for biological activity or to protect against carboxypeptidase degradation in plasma.

The target peptide is released from the fusion protein as a carboxy-terminal α-thioester, which can react with many nucleophiles via nucleophilic acyl substitution reactions and the invention therefore further provides a method for producing a wider range of peptides comprising carboxy-terminal modifications such as peptide elongation by chemical ligation, bioconjugation with biological or non-biological entities, and, amidation.

Peptide YY (PYY) and pancreatic peptide (PP) both belong to a group of peptides of the PP-fold family to which neuropeptide Y (NPY) also belongs. They are all naturally secreted as 36 amino acid peptides with a carboxy-terminal amide. They are characterised by a common three-dimensional fold, the PP-fold, which is considered as a stabilizing element important for their biological function. The amino acid sequence of human PYY(1-36) and human PP(1-36) are shown in SEQ ID NO: 2 and SEQ ID NO: 14, respectively. PP-fold peptides or analogues thereof have been suggested for use in the treatment of obesity and associated diseases based on the demonstrated anorectic effects of certain of the these peptides in animal models and in man.

By PYY is meant the human peptide hormone and species variants thereof. In one aspect, the target peptide is PYY or an analogue thereof. PYY is released during a meal from L-cells in the distal small intestine and the colon. PYY is released as PYY(1-36) but is cleaved by dipeptidyl peptidase IV (DPP IV) to PYY(3-36) which constitutes approximately 50% of the circulating PYY. PYY(3-36) is known to have peripheral effects in the GI-tract and also act centrally as a satiety signal. The terms "human PYY" and "hPYY" are intended to mean hPYY(1-36) according to SEQ ID NO: 2, or alternatively hPYY(3-36) according to SEQ ID NO: 11, which have a deletion of the amino-terminal amino acids in position 1 and 2. In one aspect the term PYY is intended to refer to human PYY. In one aspect, the target peptide is PYY(3-36). In one aspect, the target peptide is hPYY(3-36). In one aspect the target peptide is an analogue of PYY. In one aspect the target peptide is an analogue of hPYY. In one aspect, the target peptide is [Gly4]-PYY(4-36). In one aspect, the target peptide is [Gly4]-hPYY(4-36) of SEQ ID NO: 10. In one aspect, the target peptide is [Arg4, Gln18, Lys30]-PYY(3-36). In one aspect, the target peptide is [Arg4, Gln18, Lys30]-hPYY(3-36) of SEQ ID NO: 15.

In one aspect, the target peptide is PP or an analogue thereof. Pancreatic Polypeptide (PP) PP is a hormone secreted from the endocrine cells in pancreatic islets and release is stimulated by food intake. PP is known to reduce food-intake and potentially increase energy expenditure. By PP is meant the human peptide hormone and species variants thereof. In one aspect, the target peptide is PP. In one aspect the target peptide is hPP. In one aspect, the target peptide is hPP(1-36) according to SEQ ID NO: 14.

Calcitonin gene-related peptide (CGRP) is a peptide which, in several species, exists in two forms, designated α-CGRP and (3-CGRP (or CGRP-I and CGRP-II, respectively). CGRP peptides are highly conserved within species. CGRP is released from, e.g., sensory, motor and enteric nerves. CGRP triggers various pharmacological effects, e.g.: 1) vasodilation, 2) muscle and liver AMP kinase (AMPK) activation and lipolysis and/or fat oxidation, 3) reduction in food intake, 4) inhibition of gastric emptying and modification of gut function and 5) increasing glycolysis and inhibition of glycogen synthesis. Whereas AMPK activation, fat oxidation and reduced food intake may be beneficial in metabolic diseases, glycolysis and inhibition of glycogen synthesis has been suggested to mediate insulin resistance.

By α-CGRP is meant the human peptide hormone and species variants thereof. In one aspect, the target peptide is α-CGRP or an analogue thereof. In one aspect, the target peptide is α-CGRP. In one aspect, the target peptide is hα-CGRP of SEQ ID NO: 12.

Calcitonin (CT) has been used clinically for treatment of disorders of calcium metabolism and pain, and its relationship to increased glucose levels in mammals has been the subject of varying reports. The use of calcitonins in the treatment of diabetes mellitus has also been described.

Calcitonin is a small peptide produced by the parafollicular cells of the thyroid gland in mammals and by the ultimobranchial glands of birds and fish. Many types of calcitonin have been isolated, such as human calcitonin, salmon calcitonin, eel calcitonin, elkatonin, porcine calcitonin, and chicken calcitonin. There is significant structural non-homology among the various calcitonin types. For example, there is only 50% identity between the amino acids making up human calcitonin and those making up salmon calcitonin. Human calcitonin (hCT) is a peptide hormone containing 32 amino acid residues which is produced primarily by the Parafollicular (also known as C) cells of the thyroid. Salmon calcitonin is also a 32-mer polypeptide.

By "calcitonin" or "CT" is meant the human peptide hormone and species variants thereof, including human calcitonin (hCT) or salmon calcitonin (sCT). In one aspect, the target peptide is CT or an analogue thereof. In one aspect, the target peptide is CT. In one aspect, the target peptide is human CT. In one aspect, the target peptide is hCT of SEQ ID NO: 13.

In one aspect, the target peptide is amylin or an analogue thereof. Human amylin (hAmylin) is a 37 amino acid long polypeptide of SEQ ID NO: 3 that binds to two distinct receptor complexes. These two complexes contain the calcitonin receptor plus a receptor activity-modifying protein, RAMP1 or RAMP3. From the close relationship between the calcitonin receptor and the amylin receptor some cross-reactivity to the calcitonin receptor may be expected of amylin receptor agonist. The calcitonin receptor is found in many tissues throughout the body and it is believed to be involved in regulation of bone metabolism. Polypeptides with activity at the calcitonin receptor could be useful in the treatment of hypercalcaemia, osteoporosis, Pagets disease, obesity or obesity related diseases as well as in the prevention of obesity related diseases.

By amylin is meant the human peptide hormone and species variants thereof. In one aspect, the target peptide is amylin. In one aspect, the target peptide is [Asp14, Arg17, Pro21, Pro27, Arg35]-Amylin. In one aspect, the target peptide is [Asp14, Arg17, Pro21, Pro27, Arg35]-hAmylin of SEQ ID NO: 16.

In one aspect, the intein sequence is located at the carboxy-terminus of the target peptide.

The term "polypeptide" and "peptide" as used herein means a compound composed of at least five constituent amino acids connected by peptide bonds. All amino acids for which the optical isomer is not stated is to be understood to mean the L-isomer. However, also contemplated within the scope of the invention are D-amino acid residues of one or more of the amino acids.

The constituent amino acids of the peptides according to the invention may be from the group of the amino acids encoded by the genetic code and they may be natural amino acids which are not encoded by the genetic code, as well as synthetic amino acids. Natural amino acids which are not encoded by the genetic code are e.g., γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), β-alanine, 3-aminomethyl benzoic acid, anthranilic acid.

The 22 proteinogenic amino acids are: Alanine, Arginine, Asparagine, Aspartic acid, Cysteine, Cystine, Glutamine, Glutamic acid, Glycine, Histidine, Hydroxyproline, Isoleucine, Leucine, Lysine, Methionine, Phenylalanine, Proline, Serine, Threonine, Tryptophan, Tyrosine, Valine.

Thus a non-proteinogenic amino acid is a moiety which can be incorporated into a peptide via peptide bonds but is not a proteogenic amino acid. Examples are γ-carboxyglutamate, ornithine, phosphoserine, the D-amino acids such as D-alanine and D-glutamine, synthetic non-proteogenic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), 3-aminomethyl benzoic acid, anthranilic acid, des-amino-Histidine, the beta analogues of amino acids such as β-alanine etc., D-histidine, desamino-histidine, 2-amino-histidine, β-hydroxy-histidine, homohistidine, Nα-acetyl-histidine, α-fluoromethyl-histidine, α-methyl-histidine, 3-pyridylalanine, 2-pyridylalanine or 4-pyridylalanine, (1-aminocyclopropyl)carboxylic acid, (1-aminocyclobutyl)carboxylic acid, (1-aminocyclopentyl)carboxylic acid, (1-aminocyclohexyl)carboxylic acid, (1-aminocycloheptyl)carboxylic acid, or (1-aminocyclooctyl)carboxylic acid.

Unnatural amino acids for use in the invention include but is not limited to, -thiotyrosine, ornithine, 3-mercaptophenylalanine, 3- or 4-aminophenylalanine, 3- or 4-acetylphenylalanine, 2- or 3-hydroxyphenylalanine (o- or m-tyrosine), hydroxymethylglycine, aminoethylglycine, 1-methyl-1-mercaptoethylglycine, aminoethylthioethylglycine and mercaptoethylglycine. Many of the unnatural amino acids useful in the present invention are commercially available. Others may be prepared by methods known in the art.

The term "analogue" as used herein referring to a peptide means a peptide wherein at least one amino acid residue of the peptide has been substituted with another amino acid residue and/or wherein at least one amino acid residue has been deleted from the peptide and/or wherein at least one amino acid residue has been added to the peptide and/or wherein at least one amino acid residue of the peptide has been modified. Such addition, substitution or deletion of amino acid residues can take place at the amino-and/or carboxy-terminus of the peptide and/or at within the polypeptide sequence.

The term "substitution" is intended to mean the change of one amino acid in the native sequence with another amino acid.

The term "deletion" is intended to mean the removal of one or more amino acids from the native sequence.

The term "insertion" is intended to mean the addition of one or more amino acid into the native sequence.

The term "modification" is intended to mean alterations covalently attached to the side chain of one or more amino acids or the alpha nitrogen atom of one or more amino acid in the native peptide sequence.

A simple nomenclature is used to describe the peptides according to the invention, e.g., [Gly4]-hPYY(4-36) designates an analogue of the human PYY (hPYY) ID: SEQ ID NO: 2 wherein the naturally occurring lysine in position 4 has been substituted with glycine and the naturally occurring tyrosine, proline and isoleucine in position 1, 2 and 3, respectively, have been deleted. In one aspect the target peptide may be derived from vertebrates, such as a mammal, including human, mouse, sheep, goat, cow or horse. The term "vertebrate" means members of the subphylum Vertebrata, a primary division of the phylum Chordata that includes the fish, amphibians, reptiles, birds, and mammals, all of which are characterized by a segmented spinal column and a distinct well-differentiated head. The term "mammal" means humans as well as all other warm-blooded members of the animal kingdom possessed of a homeostatic mechanism in the class Mammalia, e.g., companion mammals, zoo mammals, and food-source mammals. Some examples of companion mammals are canines (e.g., dogs), felines (e.g., cats) and horses; some examples of food-source mammals are pigs, cattle, sheep, and the like. In one aspect the mammal is a human or a companion mammal. In one aspect the mammal is a human, male or female.

In a further refinement of the system the fusion protein also comprises a tag, which allows for identification and/or purification of the fusion protein, and thus the peptide, by affinity or other chromatographic methods. Examples of a suitable tag include a specific chitin-binding domain, or part thereof, a repeat of acidic or basic amino acids, glutathione transferase tags, tags recovered with antibodies such as FLAG tag, HA tag, MYC tag, biotin or streptavidin and a small polypeptide sequence containing at least five histidines, a His-tag, for immobilized metal affinity chromatography. The purification tag may also comprise a highly basic ribosomal protein derived from thermophilic bacteria as described in international patent applications published under number WO 2006/108826 and WO 2008/043847. For example, the fusion protein may include a His-tag that binds tightly to an immobilized metal ion affinity chromatography column that can be used for the affinity purification of the intact fusion protein.

In one aspect, the fusion protein further comprises a purification tag and optionally a protease site, which allows for identification and/or purification by affinity chromatography or other chromatographic methods. In one aspect, the purification tag is alkaline. In one aspect, the purification tag comprises a histidine tag. In one aspect, the purification tag and optionally protease site is located at the amino-terminus of the target peptide.

Any expression system which can operate on a commercial scale is suitable although the intein based vector described above is designed for use in $E.\ coli$. Other vectors can be designed for optimal use in a particular expression system. For example, if a mammalian expression system was chosen, then protein-encoding regions should have optimised codon usage for that particular system. Examples of expression systems which could be used to express peptide fusion proteins include bacteria ($E.\ coli$, $B.\ subtilis$ etc.), yeast ($S.\ cerevisiae$, $P.\ pastoralis$ etc.), insect cells ($S.\ frugiperda$), mammalian expression systems (chinese hamster ovary, baby hamster kidney etc.), transgenic mammalian expression in milk or other body fluids (preferably pig, cow, sheep, goat, rabbit etc). In the case of an $E.\ coli$ expression system, the initiator methionine may be retained in the expression product. One example is PYY(3-36) that has an amino-terminal isoleucine, which is not expected to result in efficient removal of the initiator methionine by methionine aminopeptidase after expression in $E.\ coli$. However, the native amino-terminal of the target peptide can be obtained by fusing the amino-terminal to a label such as a purification tag with an intervening linker containing a protease site. Subsequent removal of the purification tag by use of an appropriate protease (e.g. alp, enterokinase or human rhinovirus-14 3C (HRV14-3C)) or peptidase (e.g. dipeptidyl aminopeptidase 1 (DAP1)) will generate the native amino-terminal of the target peptide. Alternatively, the initiator methionine can be removed chemically by contacting with cyanogen bromide.

In one aspect, the fusion protein is expressed in bacteria, yeast, mammalian cells or in a body fluid of a transgenic mammal. In one aspect, the fusion protein is expressed in bacteria or yeast. In one aspect, the fusion protein is expressed in bacteria. In one aspect, the fusion protein is expressed in $E.\ coli$.

Thioesters are relatively reactive chemical groups, compared to either peptide bonds or oxygen-esters, and are therefore readily converted to amides under mild reaction conditions. The preferred reagent is MESNa but many other mercaptogroup (sulfhydryl-, thiol-group) containing reagents could also function effectively. The released MES $\alpha$-thioester is relatively stable to hydrolysis by water (which irreversibly would generate the unwanted free acid) and is suitable for reaction with any chemical conditions that will promote amide formation.

In one aspect, the method comprises thiol-induced cleavage of the fusion protein resulting in the $\alpha$-thioester of the target peptide. In one aspect, the method further comprises conversion of the $\alpha$-thioester to the corresponding $\alpha$-amide of the target peptide. In one aspect, the amidation step occurs in the presence of an ammonium nucleophile. In one aspect, the ammonium nucleophile is provided as an aqueous solution of ammonium bicarbonate.

In one aspect, the invention provides a method for producing the [Gly4]-hPYY(4-36) of SEQ ID NO: 10, which comprises the step of expressing the peptide as part of a fusion protein, wherein said fusion protein comprises a target peptide of SEQ ID NO: 10, an intein of SEQ ID NO: 20, a purification tag of SEQ ID NO: 4 and a protease site of SEQ ID NO: 8, wherein said intein sequence is located at the carboxy-terminus of the target peptide and said purification tag and protease site is located at the amino-terminus of the target peptide.

In one aspect, the invention provides a method for producing hPYY(3-36) of SEQ ID NO: 11, which comprises the step of expressing the peptide as part of a fusion protein, wherein said fusion protein comprises a target peptide of SEQ ID NO: 11, an intein of SEQ ID NO: 20, a purification tag of SEQ ID NO: 5 and a protease site of SEQ ID NO: 9, wherein said intein sequence is located at the carboxy-terminus of the target peptide and said purification tag and protease site is located at the amino-terminus of the target peptide.

In one aspect, the invention provides a method for producing h$\alpha$-CGRP of SEQ ID NO: 12, which comprises the step of expressing the peptide as part of a fusion protein, wherein said fusion protein comprises a target peptide of SEQ ID NO: 12, an intein of SEQ ID NO: 20, a purification tag of SEQ ID NO: 5 and a protease site of SEQ ID NO: 9, wherein said intein sequence is located at the carboxy-terminus of the target peptide and said purification tag and protease site is located at the amino-terminus of the target peptide.

In one aspect, the invention provides a method for producing hPP of SEQ ID NO: 14, which comprises the step of expressing the peptide as part of a fusion protein, wherein said fusion protein comprises a target peptide of SEQ ID NO: 14, an intein of SEQ ID NO: 20, a purification tag of SEQ ID NO: 5 and a protease site of SEQ ID NO: 9, wherein said intein sequence is located at the carboxy-terminus of the target peptide and said purification tag and protease site is located at the amino-terminus of the target peptide.

In one aspect, the invention provides a method for producing [Arg4, Gln18, Lys30]-hPYY(3-36) of SEQ ID NO: 15, which comprises the step of expressing the peptide as part of a fusion protein, wherein said fusion protein comprises a target peptide of SEQ ID NO: 15, an intein of SEQ ID NO: 20, and a purification tag of SEQ ID NO: 6, wherein said intein sequence is located at the carboxy-terminus of the target peptide and said purification tag is located at the amino-terminus of the target peptide.

In one aspect, the invention provides a method for producing [Asp14, Arg17, Pro21, Pro27, Arg35]-hAmylin of SEQ ID NO: 16, which comprises the step of expressing the peptide as part of a fusion protein, wherein said fusion protein comprises a target peptide of SEQ ID NO: 16, an intein of SEQ ID NO: 20, and a purification tag of SEQ ID NO: 7, wherein said intein sequence is located at the amino-terminus of the target peptide and said purification tag is located at the carboxy-terminus of the target peptide. Expression could be optimised for any of these systems, and for intracellular or extracellular production, by the appropriate selection of leader sequence, codon usage, intein or mutant thereof, and purification strategy. The skilled person will appreciate that this invention is not tied to any particular target peptide or any species as a source.

Embodiments of the Invention

Non-limiting embodiments of the invention are:

1. A method for producing a peptide, which comprises the step of expressing the peptide as part of a fusion protein, wherein said fusion protein comprises a target peptide and an intein, wherein said intein is minimized in size and carries a cysteine mutation in the position corresponding by alignment to position 3 of Mxe GyrA intein (SEQ ID NO:1).
2. A method according to embodiment 1, wherein said intein is a GyrA intein.
3. A method according to any of the preceding embodiments, wherein said intein is a Mxe GyrA intein.
4. A method according to any of the preceding embodiments, wherein said intein is a Mxe GyrA intein minimized in size by excision of residues 107-164 or a part of residues 107-164 of the Mxe GyrA intein (SEQ ID NO:1).
5. A method according to any of the preceding embodiments, wherein said intein is a Mxe GyrA intein minimized in size by excision of residues 107-164 or a part of residues 107-164 of the Mxe GyrA intein (SEQ ID NO:1) and where the excised residues are replaced by a linker comprising from 1 to 10 amino acids.
6. A method according to any of the preceding embodiments, wherein said intein is a Mxe GyrA intein minimized in size by excision of residues 107-164 or a part of residues 107-164 of the Mxe GyrA intein (SEQ ID NO:1) and where the excised residues are replaced by a linker comprising from 6 to 10 amino acids, wherein at least 6 of the amino acids of the linker are glycine and/or serine.
7. A method according to any of the preceding embodiments, wherein said intein is a Mxe GyrA intein minimized in size by excision of residues 107-164 of the Mxe GyrA intein (SEQ ID NO:1) and where the excised residues are replaced by a linker of sequence GSGSGSGS (SEQ ID NO: 34).
8. A method according to any of the preceding embodiments, wherein the sequence of said intein is SEQ ID NO: 20.
9. A method according to any of the preceding embodiments, wherein said intein sequence is located at the carboxy-terminus of the target peptide.
10. A method according to any of the preceding embodiments, wherein the target peptide is a peptide hormone involved in diabetes or obesity control.
11. A method according to any of the preceding embodiments, wherein the target peptide is a peptide hormone involved in diabetes control.
12. A method according to any of the preceding embodiments, wherein the target peptide is a peptide hormone involved in obesity control.
13. A method according to any of the preceding embodiments, wherein the target peptide is an α-amidated peptide.
14. A method according to any one of the preceding embodiments, wherein an endogenous form of the target peptide is an α-amidated peptide.
15. A method according to any of the preceding embodiments, wherein the target peptide is a carboxy-terminal bioconjugated peptide.
16. A method according to any of the preceding embodiments, wherein the target peptide is selected from PYY, PP, α-CGRP, CT and amylin or analogues thereof.
17. A method according to any of the preceding embodiments, wherein the target peptide is selected from PYY, PP, α-CGRP, and amylin or analogues thereof.
18. A method according to any one of the preceding embodiments, wherein the target peptide is PYY or an analogue thereof.
19. A method according to any one of the preceding embodiments, wherein the target peptide is hPYY or an analogue thereof.
20. A method according to any one of the preceding embodiments, wherein the target peptide is [Gly4]-PYY(4-36).
21. A method according to any one of the preceding embodiments, wherein the target peptide is [Gly4]-hPYY(4-36).
22. A method according to any one of the preceding embodiments, wherein the target peptide is PYY(3-36).
23. A method according to any one of the preceding embodiments, wherein the target peptide is hPYY(3-36).
24. A method according to any one of the preceding embodiments, wherein the target peptide is [Arg4, Gln18, Lys30]-PYY(3-36).
25. A method according to any one of the preceding embodiments, wherein the target peptide is [Arg4, Gln18, Lys30]-hPYY(3-36).
26. A method according to any one of the preceding embodiments, wherein the target peptide is α-CGRP or an analogue thereof.
27. A method according to any one of the preceding embodiments, wherein the target peptide is α-CGRP.
28. A method according to any one of the preceding embodiments, wherein the target peptide is hα-CGRP.
29. A method according to any one of the preceding embodiments, wherein the target peptide is CT or an analogue thereof.
30. A method according to any one of the preceding embodiments, wherein the target peptide is CT.
31. A method according to any one of the preceding embodiments, wherein the target peptide is hCT.
32. A method according to any one of the preceding embodiments, wherein the target peptide is PP or an analogue thereof.
33. A method according to any one of the preceding embodiments, wherein the target peptide is PP.
34. A method according to any one of the preceding embodiments, wherein the target peptide is hPP.
35. A method according to any one of the preceding embodiments, wherein the target peptide is amylin or an analogue thereof.
36. A method according to any one of the preceding embodiments, wherein the target peptide is hAmylin or an analogue thereof.

37. A method according to any one of the preceding embodiments, wherein the target peptide is [Asp14, Arg17, Pro21, Pro27, Arg35]-Amylin.
38. A method according to any one of the preceding embodiments, wherein the target peptide is [Asp14, Arg17, Pro21, Pro27, Arg35]-hAmylin.
39. A method according to any of the preceding embodiments, wherein the fusion protein further comprises a purification tag and optionally a protease site, which allows for identification and/or purification by affinity or other chromatographic methods.
40. A method according to embodiment 39, wherein the purification tag is alkaline.
41. A method according to embodiment 39 wherein the purification tag comprises a histidine tag.
42. A method according to any one of embodiments 39-41, wherein the purification tag and optionally protease site is located at the amino-terminus of the target peptide.
43. A method according to any one of the embodiments 39-42, wherein the purification tag may be cleaved off with an appropriate protease to give the target peptide.
44. A method according to any of the preceding embodiments, wherein the fusion protein is expressed in bacteria, yeast, mammalian cells or in a body fluid of a transgenic mammal.
45. A method according to any of the preceding embodiments wherein the fusion protein is expressed in bacteria or yeast.
46. A method according to any of the preceding embodiments, wherein the fusion protein is expressed in bacteria.
47. A method according to any of the preceding embodiments, wherein the fusion protein is expressed in *E. coli*.
48. A method according to any of the preceding embodiments, further comprising thiol-induced cleavage of the fusion protein resulting in the α-thioester of the target peptide.
49. A method according to embodiment 48 further comprising conversion of the α-thioester to the corresponding α-amide of the target peptide.
50. A method according to embodiment 49, wherein the amidation step occurs in the presence of an ammonium nucleophile.
51. A method according to embodiment 50, wherein the ammonium nucleophile is ammonium bicarbonate.
52. A method for producing an α-amidated peptide, which comprises the step of expressing the peptide as part of a fusion protein, wherein said fusion protein comprises a target peptide and an intein of SEQ ID NO: 20.
53. A method according to embodiment 52, wherein said intein sequence is located at the carboxy-terminus of the target peptide.
54. A method according to any of embodiments 52-53, wherein the fusion protein further comprises a purification tag and optionally a protease site, which allows for identification and/or purification by affinity or other chromatographic methods.
55. A method according to embodiment 54 wherein the purification tag comprises a histidine tag.
56. A method according to embodiment 55 wherein the purification tag comprises an alkaline tag.
57. A method according to any one of embodiments 54-56, wherein the purification tag and optionally protease site is located at the amino-terminus of the target peptide.
58. A method according to any one of the embodiments 54-57, wherein the purification tag may be cleaved off with an appropriate protease to give the target peptide.
59. A method according to any of embodiments 52-58, wherein the fusion protein is expressed in bacteria, yeast, mammalian cells or in a body fluid of a transgenic mammal.
60. A method according to embodiment 59, wherein the fusion protein is expressed in bacteria or yeast.
61. A method according to embodiment 59, wherein the fusion protein is expressed in bacteria.
62. A method according to embodiment 59, wherein the fusion protein is expressed in *E. coli*.
63. A method for producing [Gly4]-hPYY(4-36), which comprises the step of expressing the peptide as part of a fusion protein, wherein said fusion protein comprises a target peptide of SEQ ID NO: 10, an intein of SEQ ID NO: 20, a purification tag of SEQ ID NO: 4 and a protease site of SEQ ID NO: 8, and wherein said intein sequence is located at the carboxy-terminus of the target peptide and said purification tag and protease site is located at the amino-terminus of the target peptide.
64. A method for producing hPYY(3-36), which comprises the step of expressing the peptide as part of a fusion protein, wherein said fusion protein comprises a target peptide of SEQ ID NO: 11, an intein of SEQ ID NO: 20, a purification tag of SEQ ID NO: 5 and a protease site of SEQ ID NO: 9, and wherein said intein sequence is located at the carboxy-terminus of the target peptide and said purification tag and protease site is located at the amino-terminus of the target peptide.
65. A method for producing hα-CGRP, which comprises the step of expressing the peptide as part of a fusion protein, wherein said fusion protein comprises a target peptide of SEQ ID NO: 12, an intein of SEQ ID NO: 20, a purification tag of SEQ ID NO: 5 and a protease site of SEQ ID NO: 9, and wherein said intein sequence is located at the carboxy-terminus of the target peptide and said purification tag and protease site is located at the amino-terminus of the target peptide.
66. A method for producing hPP, which comprises the step of expressing the peptide as part of a fusion protein, wherein said fusion protein comprises a target peptide of SEQ ID NO: 14, an intein of SEQ ID NO: 20, a purification tag of SEQ ID NO: 5 and a protease site of SEQ ID NO: 9, and wherein said intein sequence is located at the carboxy-terminus of the target peptide and said purification tag and protease site is located at the amino-terminus of the target peptide.
67. A method for producing [Arg4, Gln18, Lys30]-hPYY (3-36), which comprises the step of expressing the peptide as part of a fusion protein, wherein said fusion protein comprises a target peptide of SEQ ID NO: 15, an intein of SEQ ID NO: 20, and a purification tag of SEQ ID NO: 6, and wherein said intein sequence is located at the carboxy-terminus of the target peptide and said purification tag is located at the amino-terminus of the target peptide.
68. A method for producing [Asp14, Arg17, Pro21, Pro27, Arg35]-hAmylin, which comprises the step of expressing the peptide as part of a fusion protein, wherein said fusion protein comprises a target peptide of SEQ ID NO: 16, an intein of SEQ ID NO: 20, and a purification tag of SEQ ID NO: 7, and wherein said intein sequence is located at the carboxy-terminus of the target peptide and said purification tag is located at the amino-terminus of the target peptide.

69. A fusion protein comprising a target peptide and an intein, wherein said intein is minimized in size and carries a cysteine mutation in the position corresponding by alignment to position 3 of Mxe GyrA intein (SEQ ID NO:1).
70. A fusion protein according to embodiment 69, wherein said intein is a GyrA intein.
71. A fusion protein according to embodiment 70 wherein said intein is a Mxe GyrA intein.
72. A fusion protein according to embodiment 71, wherein said intein is a Mxe GyrA intein minimized in size by excision of residues 107-164 or a part of residues 107-164 of the Mxe GyrA intein (SEQ ID NO:1) and where the excised residues are replaced by a linker of sequence GSGSGSGS (SEQ ID NO: 34).
73. A fusion protein according to embodiment 72, wherein said intein is a Mxe GyrA intein minimized in size by excision of residues 107-160 of the Mxe GyrA intein (SEQ ID NO:1) and where the excised residues are replaced by a linker of sequence GSGSGSGS (SEQ ID NO: 34).
74. A fusion protein according to embodiment 73, wherein the sequence of said intein is SEQ ID NO: 20.
75. A fusion protein according to any of embodiments 69-74, wherein said intein sequence is located at the carboxy-terminus of the target peptide.
76. A fusion protein according to any of embodiments 69-75, wherein the target peptide is a peptide hormone involved in diabetes or obesity control.
77. A fusion protein according to any of embodiments 69-76, wherein the target peptide is a peptide hormone involved in diabetes control.
78. A fusion protein according to any of embodiments 69-76, wherein the target peptide is a peptide hormone involved in obesity control.
79. A fusion protein according to any of embodiments 69-78, wherein the target peptide is an α-amidated peptide.
80. A fusion protein according to any of embodiments 69-78, wherein an endogenous form of the target peptide is an α-amidated peptide.
81. A fusion protein according to any of embodiments 69-78, wherein the target peptide is a carboxy-terminal bioconjugated peptide.
82. A fusion protein according to any of embodiments 69-78, wherein the target peptide is selected from PYY, PP, α-CGRP, and amylin or analogues thereof.
83. A fusion protein according to embodiment 82, wherein the target peptide is PYY or an analogue thereof.
84. A fusion protein according to embodiment 83, wherein the target peptide is hPYY or an analogue thereof.
85. A fusion protein according to embodiment 83, wherein the target peptide is [Gly4]-PYY(4-36).
86. A fusion protein according to embodiment 83, wherein the target peptide is [Gly4]-hPYY(4-36).
87. A fusion protein according to embodiment 83, wherein the target peptide is PYY(3-36).
88. A fusion protein according to embodiment 83, wherein the target peptide is hPYY(3-36).
89. A fusion protein according to embodiment 83, wherein the target peptide is [Arg4, Gln18, Lys30]-PYY(3-36).
90. A fusion protein according to embodiment 83, wherein the target peptide is [Arg4, Gln18, Lys30]-hPYY(3-36).
91. A fusion protein according to embodiment 82, wherein the target peptide is α-CGRP or an analogue thereof.
92. A fusion protein according to embodiment 91, wherein the target peptide is α-CGRP.
93. A fusion protein according to embodiment 91, wherein the target peptide is hα-CGRP.
94. A fusion protein according to embodiment 82, wherein the target peptide is CT or an analogue thereof.
95. A fusion protein according to embodiment 94, wherein the target peptide is CT.
96. A fusion protein according to embodiment 94, wherein the target peptide is hCT.
97. A fusion protein according to embodiment 82, wherein the target peptide is PP or an analogue thereof.
98. A fusion protein according to embodiment 97, wherein the target peptide is PP.
99. A fusion protein according to embodiment 97, wherein the target peptide is hPP.
100. A fusion protein according to embodiment 82, wherein the target peptide is amylin or an analogue thereof.
101. A fusion protein according to embodiment 100, wherein the target peptide is [Asp14, Arg17, Pro21, Pro27, Arg35]-Amylin.
102. A fusion protein according to embodiment 100, wherein the target peptide is [Asp14, Arg17, Pro21, Pro27, Arg35]-hAmylin.
103. A fusion protein according to any of embodiments 69-102 further comprising a purification tag and optionally a protease site, which allows for identification and/or purification by affinity or other chromatographic methods.
104. A fusion protein according to embodiment 103, wherein the purification tag is alkaline.
105. A fusion protein according to embodiment 104, wherein the purification tag comprises a histidine tag.
106. A fusion protein according to any one of embodiments 103-105, wherein the purification tag and optionally protease site is located at the amino-terminus of the target peptide.
107. A fusion protein according to any one of embodiments 103-106, wherein the purification tag may be cleaved off with an appropriate protease to give the target peptide.
108. A fusion protein comprising a target peptide of SEQ ID NO: 10, an intein of SEQ ID NO: 20, a purification tag of SEQ ID NO: 4 and a protease site of SEQ ID NO: 8, wherein said intein sequence is located at the carboxy-terminus of the target peptide and said purification tag and protease site is located at the amino-terminus of the target peptide.
109. A fusion protein comprising a target peptide of SEQ ID NO: 11, an intein of SEQ ID NO: 20, a purification tag of SEQ ID NO: 5 and a protease site of SEQ ID NO: 9, wherein said intein sequence is located at the carboxy-terminus of the target peptide and said purification tag and protease site is located at the amino-terminus of the target peptide.
110. A fusion protein comprising a target peptide of SEQ ID NO: 12, an intein of SEQ ID NO: 20, a purification tag of SEQ ID NO: 5 and a protease site of SEQ ID NO: 9, wherein said intein sequence is located at the carboxy-terminus of the target peptide and said purification tag and protease site is located at the amino-terminus of the target peptide.
111. A fusion protein comprising a target peptide of SEQ ID NO: 14, an intein of SEQ ID NO: 20, a purification tag of SEQ ID NO: 5 and a protease site of SEQ ID NO: 9, wherein said intein sequence is located at the carboxy-terminus of the target peptide and said purification tag and protease site is located at the amino-terminus of the target peptide.

112. A fusion protein comprising a target peptide of SEQ ID NO: 15, an intein of SEQ ID NO: 20, and a purification tag of SEQ ID NO: 6, wherein said intein sequence is located at the carboxy-terminus of the target peptide and said purification tag is located at the amoino-terminus of the target peptide.

113. A fusion protein comprising a target peptide of SEQ ID NO: 16, an intein of SEQ ID NO: 20, and a purification tag of SEQ ID NO: 7, wherein said intein sequence is located at the carboxy-terminus of the target peptide and said purification tag is located at the amino-terminus of the target peptide.

114. An intein which is minimized in size and carries a cysteine mutation in the position corresponding by alignment to position 3 of Mxe GyrA intein (SEQ ID NO:1).

115. An intein according to embodiment 114, wherein said intein is a GyrA intein.

116. An intein according to embodiment 115, wherein said intein is a Mxe GyrA intein.

117. An intein according to embodiment 116, wherein said intein is a Mxe GyrA intein minimized in size by excision of residues 107-164 or a part of residues 107-164 of the Mxe GyrA intein (SEQ ID NO:1) and where the excised residues are replaced by a linker of sequence GSGSGSGS (SEQ ID NO: 34).

118. An intein according to embodiment 117, wherein said intein is a Mxe GyrA intein minimized in size by excision of residues 107-160 of the Mxe GyrA intein (SEQ ID NO:1) and where the excised residues are replaced by a linker of sequence GSGSGSGS (SEQ ID NO: 34).

119. An intein according to embodiment 118, wherein the sequence of said intein is SEQ ID NO: 20.

120. An intein of SEQ ID NO: 20.

121. A DNA construct coding for a fusion protein as defined in any one of embodiments 69-113.

122. A DNA construct of embodiment 121 which is in the form of a vector.

EXAMPLES

The examples of the invention are based on human variants of PYY (hPYY), PP (hPP), amylin (hAmylin), CT (hCT), and α-CGRP (hα-CGRP). The Mxe GyrA intein variant referred to as the native intein (SEQ ID NO: 17) carries a N198A mutation, disabling its natural self-splicing function and rendering it susceptible for intermolecular thiol-induced cleavage. Seven sets of plasmids comprising a total of 35 vectors were designed (Table 1).

TABLE 1

List of fusion proteins with respective numbers as they are referred to in the examples.

| Protein no. | Plasmid no. | N-terminal tag | Protease site | Target peptide | Intein |
|---|---|---|---|---|---|
| 1A | p1A | SEQ ID NO: 4 | SEQ ID NO: 8 | SEQ ID NO: 10 | SEQ ID NO: 17 |
| 1B | p1B | SEQ ID NO: 4 | SEQ ID NO: 8 | SEQ ID NO: 10 | SEQ ID NO: 19 |
| 1C | p1C | SEQ ID NO: 4 | SEQ ID NO: 8 | SEQ ID NO: 10 | SEQ ID NO: 20 |
| 1D | p1D | SEQ ID NO: 4 | SEQ ID NO: 8 | SEQ ID NO: 10 | SEQ ID NO: 18 |
| 1E | p1E | SEQ ID NO: 4 | SEQ ID NO: 8 | SEQ ID NO: 10 | SEQ ID NO: 21 |
| 1F | p1F | SEQ ID NO: 4 | SEQ ID NO: 8 | SEQ ID NO: 10 | SEQ ID NO: 22 |
| 1G | p1G | SEQ ID NO: 4 | SEQ ID NO: 8 | SEQ ID NO: 10 | SEQ ID NO: 23 |
| 1H | p1H | SEQ ID NO: 4 | SEQ ID NO: 8 | SEQ ID NO: 10 | SEQ ID NO: 24 |
| 1I | p1I | SEQ ID NO: 4 | SEQ ID NO: 8 | SEQ ID NO: 10 | SEQ ID NO: 25 |
| 1J | p1J | SEQ ID NO: 4 | SEQ ID NO: 8 | SEQ ID NO: 10 | SEQ ID NO: 26 |
| 1K | p1K | SEQ ID NO: 4 | SEQ ID NO: 8 | SEQ ID NO: 10 | SEQ ID NO: 27 |
| 1L | p1L | SEQ ID NO: 4 | SEQ ID NO: 8 | SEQ ID NO: 10 | SEQ ID NO: 28 |
| 1M | p1M | SEQ ID NO: 4 | SEQ ID NO: 8 | SEQ ID NO: 10 | SEQ ID NO: 29 |
| 1N | p1N | SEQ ID NO: 4 | SEQ ID NO: 8 | SEQ ID NO: 10 | SEQ ID NO: 30 |
| 1O | p1O | SEQ ID NO: 4 | SEQ ID NO: 8 | SEQ ID NO: 10 | SEQ ID NO: 31 |
| 1P | p1P | SEQ ID NO: 4 | SEQ ID NO: 8 | SEQ ID NO: 10 | SEQ ID NO: 32 |
| 1Q | p1Q | SEQ ID NO: 4 | SEQ ID NO: 8 | SEQ ID NO: 10 | SEQ ID NO: 33 |
| 2A | p2A | SEQ ID NO: 5 | SEQ ID NO: 9 | SEQ ID NO: 11 | SEQ ID NO: 17 |
| 2B | p2B | SEQ ID NO: 5 | SEQ ID NO: 9 | SEQ ID NO: 11 | SEQ ID NO: 19 |
| 2C | p2C | SEQ ID NO: 5 | SEQ ID NO: 9 | SEQ ID NO: 11 | SEQ ID NO: 20 |
| 3A | p3A | SEQ ID NO: 5 | SEQ ID NO: 9 | SEQ ID NO: 12 | SEQ ID NO: 17 |
| 3B | p3B | SEQ ID NO: 5 | SEQ ID NO: 9 | SEQ ID NO: 12 | SEQ ID NO: 19 |
| 3C | p3C | SEQ ID NO: 5 | SEQ ID NO: 9 | SEQ ID NO: 12 | SEQ ID NO: 20 |
| 4A | p4A | SEQ ID NO: 5 | SEQ ID NO: 9 | SEQ ID NO: 13 | SEQ ID NO: 17 |
| 4B | p4B | SEQ ID NO: 5 | SEQ ID NO: 9 | SEQ ID NO: 13 | SEQ ID NO: 19 |
| 4C | p4C | SEQ ID NO: 5 | SEQ ID NO: 9 | SEQ ID NO: 13 | SEQ ID NO: 20 |
| 5A | p5A | SEQ ID NO: 5 | SEQ ID NO: 9 | SEQ ID NO: 14 | SEQ ID NO: 17 |
| 5B | p5B | SEQ ID NO: 5 | SEQ ID NO: 9 | SEQ ID NO: 14 | SEQ ID NO: 19 |
| 5C | p5C | SEQ ID NO: 5 | SEQ ID NO: 9 | SEQ ID NO: 14 | SEQ ID NO: 20 |
| 6A | p6A | SEQ ID NO: 6 | | SEQ ID NO: 15 | SEQ ID NO: 17 |
| 6B | p6B | SEQ ID NO: 6 | | SEQ ID NO: 15 | SEQ ID NO: 19 |
| 6C | p6C | SEQ ID NO: 6 | | SEQ ID NO: 15 | SEQ ID NO: 20 |
| 7A | p7A | SEQ ID NO: 7 | | SEQ ID NO: 16 | SEQ ID NO: 17 |
| 7B | p7B | SEQ ID NO: 7 | | SEQ ID NO: 16 | SEQ ID NO: 19 |
| 7C | p7C | SEQ ID NO: 7 | | SEQ ID NO: 16 | SEQ ID NO: 20 |

Materials and Methods
List of Abbreviations
  Amp Ampicillin
  E. coli Escherichia coli
  GyrA DNA GyraseA intein from *Mycobacterium* Xenopi
  hα-CGRP Human α-calcitonin gene-related peptide hAmylin Human amylin
hCT Human calcitonin
HPLC High performance liquid chromatograpy
hPP Human pancreatic peptide
hPYY Human peptide YY
IB Inclusion bodies
IPTG Isopropyl β-D-1-thiogalactopyranoside
LB Luria-Bertani
LC-MS Liquid chromatography mass spectrometry
MESNa Sodium 2-mercaptoethanesulfonate
$OD_{600}$ Optical density at 600 nm
RP-UPLC Reversed phase ultra performance liquid chromatography
SDS-PAGE Sodium dodecylsulfate polyacrylamide gel electrophoresis
TAP Thermostable Alkaline Protein
TFA Trifluoroacetic acid
*T. Maritima* Thermotoga Maritima General Methods of Preparation of Fusion Proteins
Cloning of Constructs:

The plasmids were either generated by cloning of synthetic gene fragments obtained from Geneart (Regensburg, Germany) into a pET11a vector (Novagen) using XhoI/BamHI, NheI/BamHI or NheI/NsiI restriction enzyme sites and T4 DNA ligase (New England BioLabs, Ipswich, Mass.) by methods described by the manufacturer or provided by Geneart as sub-cloned vectors. In either case the gene encoding the fusion proteins had been codon optimized for expression in *E. coli*. The vector map of the plasmids is exemplified in FIG. 1.

The plasmids were used to transform competent TOP10 (Invitrogen) *E. coli* cells and incubated overnight on LB medium agar plates containing 100 μg/ml Ampicillin. Plasmids encoding the respective proteins of interest were obtained from positive clones following plasmid propagation in liquid LB/Amp (100 μg/ml Ampicillin) medium and standard mini-preparations. Correctness of the nucleotide sequences were verified by DNA sequencing using T7 promoter/terminator sequence specific primers (performed by Eurofins MWG Operon, Ebersberg, Germany).

Expression of Fusion Proteins in Shake-Flasks:

Plasmids were transformed into *E. coli* expression strain BL21(DE3), which were plated on LB/Amp plates and incubated at 37° C. overnight. BL21(DE3) cells containing the appropriate plasmid were grown to $OD_{600}$ of 0.4-0.6 at 37° C. in LB/Amp medium using shaker flasks. The cells were induced with 0.5 mM IPTG at 37° C. for 3 h. Following induction, the cells were harvested by centrifugation (4000× g, 4° C., 15 min, Heraeus Multifuge 3 S-R, DJB Labcare Ltd., Newport Pagnell, England). The harvested cells were lysed by sonication (40% power with pulses of 15 sec on and off for 20 min performed on ice, Bandelin Sonopuls, Buch og Holm) in 25 mM sodium phosphate pH 5 buffer. The insoluble proteins were spun down (4000×g, 4° C., 15 min) and the cell lysate decanted.

SDS-PAGE Analysis:

Coomassie stained SDS-PAGE analysis was carried out of lysate samples in sample buffer (BioRad XT sample buffer+ 4 mM TCEP) containing induced and uninduced cells, as well as soluble and insoluble fractions of induced cells (obtained by ultrasonication and centrifugation in a buffer containing 25 mM sodium phosphate pH 5 buffer). Band intensities of fusion proteins and inteins were estimated by densitometric analysis of SDS-PAGE gels using ImageJ.

General Methods of Detection and Characterization
UPLC method A: Quantification of Fusion Proteins The protein concentration of the fusion proteins was quantified by RP-UPLC using the Acquity UPLC System (Waters) and reference Std 1 (purified fusion protein 1B, 0.169 mg/ml). The samples were analyzed using an Acquity UPLC BEH300 C4 (1.7 um, 2.1×100 mm, 1.7 μm)(Waters) column and a gradient elution using 0.1% TFA water (Eluent A) and 0.08% TFA in acetonitrile (Eluent B) at 0.4 ml/min and a column temperature of 40° C. with 214 nm detection as follows:

| Time (min) | % Eluent B |
| --- | --- |
| 0 | 20 |
| 5 | 20 |
| 20 | 60 |
| 20.5 | 99 |
| 23 | 99 |
| 23.1 | 20 |
| 26 | 20 |

A sample set was initiated with single injection of Std 1 to control the system and end with double injection of Std 1 for calibration of samples.

UPLC Method B: Analysis of Thiol-induced Cleavage

Aliquots collected from cleavage reactions of the fusion proteins were analysed by RP-UPLC using the Acquity UPLC System (Waters) and an Acquity UPLC BEHC18, (2.1×150 mm column, 1.7 μm, Waters) column connected to a BEH C18 (2.1×5 mm 1.7 μm, Waters) van guard™ pre column. A two step gradient elution using 0.1% TFA water (Eluent A) and 0.08% TFA in acetonitrile (Eluent B) at 0.4 ml/min and a column temperature of 50° C. with 214 nm detection was applied as follows:

| Time (min) | % Eluent B |
| --- | --- |
| 0 | 28 |
| 2 | 28 |
| 12 | 33 |
| 23 | 53 |
| 23.1 | 99 |
| 24.9 | 99 |
| 25 | 28 |
| 27 | 28 |

UPLC Method C: Quantification of Peptide α-Thioester

The concentration of α-thioester was quantified by RP-UPLC using the Acquity UPLC System (Waters) and reference Std 2 (purified peptide α-thioester of fusion protein 1A, 0.144 mg/ml). An Acquity UPLC BEHC18, (2.1×150 mm column, 1.7 μm, Waters) column connected to a BEH C18 (2.1×5 mm 1.7 μm, Waters) van guard™ pre column was applied. A linear gradient elution of 0.1% TFA water (Eluent A) and 0.08% TFA in acetonitrile (Eluent B) at 0.4 ml/min and a column temperature of 50° C. with 214 nm detection was used as follows:

| Time (min) | % Eluent B |
| --- | --- |
| 0 | 28 |
| 2 | 28 |
| 12 | 33 |
| 12.1 | 90 |
| 13.5 | 28 |
| 15.0 | 28 |

A sample set was ended with double injection of Std 2 for calibration of samples.

LC-MS Analysis A: Characterization of Fusion Proteins and Inteins

Characterisation of fusion proteins and cleavage mixtures were performed by LC-MS analysis using a LC-MSD-TOF (Agilent Technologies) instrument using a Zorbax 300SB-C18 rapid resolution (2.1×50 mm, 3.5 μm, Agilent Technologies) column and a column temperature of 40° C. MS ionisation mode was set to positive ion. Scan 100-3000 amu. A linear gradient of 8.8 mM ammonium format in 0.1% formic acid in water (Eluent A) and 0.1% formic acid in acetonitrile (Eluent B) with a flow of 0.3 ml/min and detection at 214 nm was used as follows:

| Time (min) | % Eluent B |
|---|---|
| 0 | 18 |
| 2 | 18 |
| 3 | 25 |
| 13 | 65 |
| 13.1 | 90 |
| 17 | 90 |
| 17.1 | 18 |
| 20 | 18 |

LC-MS Analysis B: Analysis of Enzymatic Cleavages

The enzymatic digestion with proteolytic enzyme to remove purification tags was analyzed by LC-MS analysis using a LC-MSD-TOF (Agilent Technologies) instrument and a Zorbax 300SB-C18 rapid resolution (2.1×50 mm, 3.5 μm, Agilent Technologies) column with a column temperature of 40° C. MS ionisation mode was set to positive ion. Scan 100-3000 amu. A linear gradient of 8.8 mM ammonium format in 0.1% formic acid in water (Eluent A) and 0.1% formic acid in acetonitrile (Eluent B) with a flow of 0.3 ml/min and detection at 214 nm was used as follows:

| Time (min) | % Eluent B |
|---|---|
| 0 | 5 |
| 3 | 5 |
| 18 | 70 |
| 18.1 | 90 |
| 22 | 90 |
| 22.1 | 5 |
| 25 | 5 |

Example 1

Measured Activities of Engineered Inteins

The objective was to generate a functional Mxe GyrA intein that was minimized in size and carried a T3C mutation. To achieve this, a set of seventeen fusion proteins that each carried a different Mxe GyrA intein variant were generated and the rate constants of their thiol-induced cleavage reactions were used as a measure for the intein activity.

All seventeen fusion proteins (protein 1A-1Q, Table 1) comprised the target peptide [Gly4]-hPYY(4-36) (SEQ ID NO: 10) fused between an amino-terminal extension via a protease site and a carboxy-terminal Mxe GyrA intein variant. The amino-terminal extension was a variant of ribosomal protein L27 from *Thermotoga maritime* (RL27tm, SEQ ID NO: 4) that allows purification by cation exchange chromatography. The protease site (SEQ ID NO: 8) contained the EVLFQ sequence that is recognized by the HRV14-3C protease and allows removal of the amino-terminal extension. Protein 1A contained the native Mxe GyrA intein variant, protein 1D contained the [Cys3]-Mxe GyrA intein variant, protein 1B and 1E-1S contained a minimized Mxe GyrA intein variant, and protein 1C contained a minimized Mxe GyrA intein variant with the T3C mutation. The minimized inteins had 46-57 amino acids between the amino- and carboxy-termini splicing regions removed or substituted with a small linker (Table 2). More specifically, the removed region comprised a part of residues 103-164 of the Mxe GyrA intein, which according to the crystal structure (Klabunde T. (1998) *Nature Structural Biology*, 5, 31-36) are located between β-strands 9 and 10 of the carboxy-terminal splicing region. The examined linkers involved the LDRHGN (SEQ ID NO: 35) sequence that links β-strand 4 and 5 of the N-terminal splicing domain of the Mxe GyrA intein, an α-helical ADNLALA (SEQ ID NO: 36) linker sequence from the linker database (George RA. and Heringa J. (2002) *Protein Engineering*, 15, 871-879), the RDVETGE (SEQ ID NO: 37) linker that links β-strand 9 and 10 of the hedgehog protein of *Drosophila melanogaster* (as described by Hiraga, K. et al. (2005) *J. Mol. Biol.* 354, 916-926), and a flexible GSGSGSGS (SEQ ID NO: 34) linker.

Table 2. List of intein variants with respective deletion size, linker and mutations.

TABLE 2

List of intein variants with respective deletion size, linker and mutations.

| Protein No | SEQ ID NO | Deletion sites[a] N-terminal | C-terminal | Linker | Mutation | Size (Residues) |
|---|---|---|---|---|---|---|
| 1A | 17 | | | | | 198 |
| 1B | 19 | Gln106 | Phe161 | GSGSGSGS (SEQ ID NO: 34) | | 152 |
| 1C | 20 | Gln106 | Phe161 | GSGSGSGS (SEQ ID NO: 34) | T3C | 152 |
| 1D | 18 | | | | T3C | 198 |
| 1E | 21 | Ser111 | Asp158 | | | 152 |
| 1F | 22 | Gln106 | Phe161 | | | 144 |
| 1G | 23 | Ser111 | Asp158 | LDRHGN (SEQ ID NO: 35) | | 158 |
| 1H | 24 | Gln106 | Phe161 | LDRHGN (SEQ ID NO: 35) | | 150 |
| 1I | 25 | Gln106 | Phe161 | RDVETGE (SEQ ID NO: 37) | | 151 |
| 1J | 26 | Gln106 | Phe161 | ADNLALA (SEQ ID NO: 36) | | 151 |
| 1K | 27 | Gln106 | Phe161 | GRGSGRGS (SEQ ID NO: 34) | | 152 |
| 1L | 28 | Ile105 | Phe161 | GSGSGSGS (SEQ ID NO: 34) | | 151 |
| 1M | 29 | Val104 | Phe161 | GSGSGSGS (SEQ ID NO: 34) | | 150 |

TABLE 2-continued

List of intein variants with respective deletion size, linker and mutations.

| Protein No | SEQ ID NO | Deletion sites[a] | | | Mutation | Size (Residues) |
|---|---|---|---|---|---|---|
| | | N-terminal | C-terminal | Linker | | |
| 1N | 30 | Ala103 | Phe161 | GSGSGSGS (SEQ ID NO: 34) | | 149 |
| 1O | 31 | Gln106 | Tyr162 | GSGSGSGS (SEQ ID NO: 34) | | 151 |
| 1P | 32 | Gln106 | Tyr163 | GSGSGSGS (SEQ ID NO: 34) | | 150 |
| 1Q | 33 | Gln106 | Ala164 | GSGSGSGS (SEQ ID NO: 34) | | 149 |

[a]Both residues are remaining as part of the truncated intein variants.

Thiol-induced Cleavage of Fusion Proteins:

The fusion proteins 1A to 1Q were expressed in shake-flasks containing 200 mL LB medium as described in the general methods. The insoluble-proteins were washed twice with MQ, divided into smaller fractions and stored at −20° C. The insoluble protein pellets were re-suspended in solubilisation buffer [100 mM sodium phosphate, pH 7.5, 5 M urea] and incubated on ice for 1 h followed by filtration (0.45 µm). The protein concentrations were determined by RP-UPLC method A, followed by dilution to a final concentration of 0.6 mg/ml with solubilisation buffer. Aliquots of the protein solutions (325 µL) were refolded by dilution into a mixture of 485 µL aqueous dilution buffer A [100 mM sodium phosphate, pH 7.5, 250 mM NaCl] and 190 µL buffer B [100 mM sodium phosphate pH 7.5, 2M urea, 150 mM NaCl], resulting in a final concentration of 0.2 mg/ml protein in 100 mM sodium phosphate, pH 7.5, 2 M urea, 150 mM NaCl. Cleavage was induced by addition of MESNa to 100 mM from a 2 M stock in buffer B. Reaction was allowed at 5° C. in an Eppendorf tube overnight with agitation (300 rpm). Aliquots were collected over time and quenched with one volume of 1.7% HCl in 6 M guanidine hydrochloride to approximately pH 3 and analyzed by RP-UPLC method B and characterized by LC-MS method A. Triplicate determination was performed and product formation was calculated as area$_{\alpha\text{-thioester product}}$/(area$_{\alpha\text{-thioester product}}$+area$_{protein}$) with α-thioester product being the amino-terminal tagged [Gly4]-PYY(4-36) α-thioester and protein being the fusion protein. Product formation was plotted as a function of time. Pseudo-first order reactions were achieved by using MESNa in great molar excess and rate constants ($k_{obs}$) were determined by fitting the data to the equation $P=P_0(1-e^{-kt})$, where P is the percentage of formed peptide α-thioester product at time t, $P_0$ is the maximum percentage of peptide α-thioester product obtained, and k is the observed rate using GraphPad Prism 5.01(GraphPad Software Inc., La Jolla, Calif.).

1.1. Measured Activities of the Functional Minimized Intein:

Initially, the Mxe GyrA intein was optimized with respect to its size. The truncated intein variants had as a minimum 46 residues removed between Ala103 and Ala164 of the Mxe GyrA intein sequence (corresponding to 23% of the overall intein size). Removal of residues 112-157 (46 amino acids) of the intein (SEQ ID NO: 21) in protein 1E reduced the splicing activity slightly compared to protein 1A, whereas removal of residues 107-160 (54 amino acids) of the intein (SEQ ID NO: 22) in protein 1F resulted in an inactive intein (Table 3). The difference on protein 1E and 1F is that the intein of protein 1E has some unstructured amino acids remaining between β-strands 9 and 10, whereas the entire unstructured region between β-strands 9 and 10 has been removed in protein 1F. Introduction of a flexible GSGSGSGS (SEQ ID NO: 34) linker between residues Gln106 and Phe161 of the intein in protein 1F, resulting in protein 1B containing an engineered intein sequence with SEQ ID NO: 19, resulted in a regain of activity to a level that was comparable to the native intein of protein 1A (Table 3). To examine if the intein in protein 1B could be even further minimized, residues at either side of the GSGSGSGS (SEQ ID NO: 34) linker was systematically removed, resulting in six fusion proteins 1N-1S. In protein 1L, 1M and 1N, one, two and three amino acids, respectively, was removed amino-terminally to the GSGSGSGS (SEQ ID NO: 34) linker of the intein (SEQ ID NO: 28-30) and this caused significant decreases in intein activity with no cleavage observed for protein 1N (Table 3). In contrast, compared to protein 1B moderate 1.1-, 1.2- and 1.7-fold drops in activity were observed for inteins (SEQ ID NO: 31-33) in protein 1O, 1P and 1Q, respectively, in which one to three amino acids had been removed carboxy-terminally to the GSGSGSGS (SEQ ID NO: 34) linker of the intein.

To evaluate the effect of differences in structural integrity and charge of the linker region a range of other linkers were inserted between the deletion sites. In protein 1G and 1H, the LDRHGN (SEQ ID NO: 35) linker was inserted between Asp158 and Ser 111 (SEQ ID NO: 23) or Gln106 and Phe 161 (SEQ ID NO: 24) of the intein, respectively. Compared to the corresponding inteins of protein 1E and 1F, where no linker was present, the LDRHGN (SEQ ID NO: 35) linker of protein 1G and 1H did not alter the intein activity (Table 3). When the hedgehog RDVETGE (SEQ ID NO: 37) linker (in SEQ ID NO: 25), an α-helical ADNLALA (SEQ ID NO: 36) linker (in SEQ ID NO: 26) or an alkaline GRGSGRGS (SEQ ID NO: 38) linker (in SEQ ID NO: 27) was introduced in place of the GSGSGSGS (SEQ ID NO: 34) linker of protein 1B, resulting in protein 1I, 1J and 1K, respectively, the intein activity was reduced by moderate 1.8-, 4.8- and 1.5-fold (Table 3).

The most active minimized intein was the one in protein 1B in which residues 107-160 had been substituted with a GSGSGSGS (SEQ ID NO: 34) linker (in SEQ ID NO: 19).

1.2. Introducing a T3C Mutation into the Minimized Intein:

Next, a T3C mutation was introduced into the minimized intein of protein 1B, resulting in protein 1C, which contained the [Cys3, 106(GS)$_4$161]-Mxe GyrA (SEQ ID NO: 20). The full length T3C intein variant, [Cys3]-Mxe GyrA (SEQ ID NO: 18), in protein 1D was used as a control. The T3C mutation of proteins 1D and 1C, respectively, resulted in a decreased intein activity compared to the native intein of protein 1A (Table 3). The decrease in activity was more pronounced for the minimized intein in protein 1C than for the full length intein in protein 1D.

Several active Mxe GyrA intein variants that were reduced in size by approximately 25% were identified. These minimized inteins had 46-57 amino acids between Gln106 and Phe161 removed or substituted with a linker. The most active minimized intein was [106(GS)$_4$161]-Mxe GyrA (SEQ ID NO: 19) that had a flexible GSGSGSGS (SEQ ID NO: 34) linker introduced instead of residues 107-160. The corresponding intein with a T3C mutation, [Cys3, 106(GS)$_4$161]-Mxe GyrA (SEQ ID NO: 20), was also active, but resulted in slower thiol-induced cleavage.

area$_{intein}$) and the relative expression level represents the area of fusion proteins A and B relative to area of fusion protein C within each group. Percentage solubility was estimated from the soluble and insoluble fractions and were calculated as area$_{soluble\ protein}$/(area$_{soluble\ protein}$+

TABLE 3

List of molecular weights of fusion proteins and their corresponding intein variants. Reaction rates of thiol-induced cleavages are further listed.

| Protein | Molecular weights | | | | Cleavage activity |
|---|---|---|---|---|---|
| | Protein | | Intein | | |
| no | Calculated (Da) | Observed (Da) | Observed (Da) | Calculated (Da) | $k_{obs}$ (s$^{-1}$) |
| 1A | 33442.5 | 33442.5 | 21269.9 | 21269.8 | $(1.0 \pm 0.1) \times 10^{-3}$ |
| 1B | 28220.2 | 28219.6 | 16047.1 | 16047.3 | $(8.6 \pm 0.5) \times 10^{-4}$ |
| 1C | 28222.2 | 28223.0 | 16049.5 | 16049.3 | $(7.6 \pm 0.4) \times 10^{-5}$ |
| 1D | 33444.5 | 33444.8 | 21271.8 | 21271.6 | $(2.5 \pm 0.2) \times 10^{-4}$ |
| 1E | 28520.6 | 28520.0 | 16347.3 | 16347.7 | $(7.0 \pm 0.5) \times 10^{-4}$ |
| 1F | 27643.7 | 27643.2 | 15470.8 | n.d. | n.d.$^a$ |
| 1G | 29213.3 | 29912.7 | 17040.1 | 17040.4 | $(7.7 \pm 0.5) \times 10^{-4}$ |
| 1H | 28336.4 | 28335.8 | 16163.5 | n.d. | n.d.$^a$ |
| 1I | 28430.5 | 28430.0 | 16257.2 | 16257.6 | $(4.7 \pm 0.2) \times 10^{-4}$ |
| 1J | 28312.4 | 28311.8 | 16139.2 | 16139.5 | $(1.8 \pm 0.1) \times 10^{-4}$ |
| 1K | 28358.4 | 28357.8 | 16185.5 | n.d. | $(5.6 \pm 0.4) \times 10^{-4}$ |
| 1L | 28092.0 | 28091.6 | 15919.0 | 15919.2 | $(4.2 \pm 0.1) \times 10^{-4}$ |
| 1M | 27978.9 | 27978.4 | 15806.0 | 15805.8 | $(5.4 \pm 0.3) \times 10^{-5}$ |
| 1N | 27879.8 | 27879.3 | 15706.9 | n.d. | n.d.$^a$ |
| 1O | 28073.0 | 28072.5 | 15900.0 | 15900.1 | $(7.9 \pm 0.4) \times 10^{-4}$ |
| 1P | 27909.8 | 27909.4 | 15736.8 | 15736.9 | $(6.9 \pm 0.2) \times 10^{-4}$ |
| 1Q | 27746.6 | 27746.2 | 15573.4 | 15573.8 | $(5.1 \pm 0.3) \times 10^{-4}$ |

$^a$No or negligible cleavage observed.

Example 2

Protein Expression Levels using an Engineered Intein

The objective was to determine how the engineered intein, [Cys3, 106(GS)$_4$161]-Mxe GyrA (SEQ ID NO: 20), affected the expression level of fusion proteins containing desired target peptides.

For each of the target peptides, [Gly4]-hPYY(4-36) (SEQ ID NO: 10), hPYY(3-36) (SEQ ID NO: 11), hα-CGRP (SEQ ID NO: 12), hCT (SEQ ID NO: 13), hPP (SEQ ID NO: 14), [Arg4, Gln18, Lys30]-hPYY(3-36) (SEQ ID NO: 15), and [Asp14, Arg17, Pro21, Pro27, Arg35]-hAmylin (SEQ ID NO: 16), three different fusion proteins were constructed. All fusion proteins were comprised of an amino-terminal extension, the target peptide, and a Mxe GyrA intein variant. A, B and C fusion proteins of each of the respective target peptides contained the native Mxe GyrA (SEQ ID NO: 17), [106(GS)$_4$161]-Mxe GyrA (SEQ ID NO: 19), and [Cys3, 106(GS)$_4$161]-Mxe GyrA (SEQ ID NO: 20) inteins, respectively.

Expression of Fusion Proteins:

BL21(DE3) cells containing the appropriate plasmids were grown in LB media (100 μg/mL ampicillin) using TPP cell suspension tubes at 37° C. to OD$_{600}$ of approximately 0.4. The cell cultures were cooled to 18° C. for 20-30 min and expression of fusion proteins were induced by adding 0.5 mM IPTG at OD$_{600}$ of 0.4-0.6. Protein expression was allowed at 18° C. over night. The cells were harvested in 1 mL aliquots by centrifugation. SDS-PAGE analysis was carried out as described in the general methods. Percentage hydrolysis and expression level were estimated from band intensities of the induced lysate samples (Table 4). Specifically, hydrolysis was calculated as area$_{intein}$/(area$_{protein}$+area$_{insoluble\ protein}$) with area$_{soluble\ protein}$ and area$_{insoluble\ protein}$ representing the total area of intein and fusion protein in the soluble and insoluble samples, respectively.

2.1. Expression of PYY-intein Fusion Proteins

The protein 1 family comprising proteins 1A, 1B, and 1C include [Gly4]-hPYY(4-36) fused between an amino-terminal extension (containing an alkaline tag (SEQ ID NO: 4) via a HRV14-3C protease site (SEQ ID NO: 8)) and a carboxy-terminal Mxe GyrA intein variant being native Mxe GyrA (SEQ ID NO: 17), [106(GS)$_4$161]-Mxe (SEQ ID NO: 19), and [Cys3, 106(GS)$_4$161]-Mxe GyrA (SEQ ID NO: 20), respectively. Proteins 1A-1C were predominantly obtained in the soluble fraction (Table 4). Approximately 50% of protein 1A and protein 1B was hydrolysed, whereas no hydrolysis was observed for the engineered intein in protein 1C. The absence of hydrolysis was associated with approximately 30% increased expression level for protein 1C compared to proteins 1A and 1B.

The protein 2 family comprising 2A, 2B, and 2C include hPYY(3-36) fused between an amino-terminal extension (containing a His tag (SEQ ID NO: 5) via an enterokinase protease site (SEQ ID NO: 9)) and a carboxy-terminal Mxe GyrA intein variant being native Mxe GyrA, [106(GS)$_4$161]-Mxe GyrA, and [Cys3, 106(GS)$_4$161]-Mxe GyrA, respectively. Proteins 2A-2C were predominantly obtained in the soluble fraction (Table 4). Approximately 60% and 50% of protein 2A and 2B was hydrolysed, respectively, whereas no hydrolysis was observed for protein 2C. This was associated with a 30-40% increase in expression level of protein 2C compared to 2A and 2B.

The protein 6 family comprising 6A, 6B, and 6C include [Arg4, Gln18, Lys30]-hPYY(3-36) fused between an amino-terminal histidine rich dodecapeptide extension that can be removed by DAP1 (SEQ ID NO: 6) and a carboxy-terminal Mxe GyrA, [106(GS)$_4$161]-Mxe GyrA, and [Cys3, 106(GS)$_4$161]-Mxe GyrA, respectively. All three fusion proteins were mainly obtained in the soluble fraction (Table 4). Approximately 50% of proteins 6A and 6B werewere hydrolysed, whereas no hydrolysis was observed for protein 6C. This was further associated with a 15-30% decreased expression level of protein 6A and 6B relative to 6C.

2.2. Expression of α-CGRP-intein Fusion Proteins

The protein 3 family comprising 3A, 3B, and 3C include hα-CGRP fused between an amino-terminal extension (containing a His tag (SEQ ID NO: 5) and an enterokinase protease site (SEQ ID NO: 9)) and a carboxy-terminal Mxe GyrA intein variant being native Mxe GyrA, [106(GS)$_4$161]-Mxe GyrA, and [Cys3, 106(GS)$_4$161]-Mxe GyrA, respectively. All three fusion proteins were mainly obtained in the soluble fraction (Table 4). Approximately 50% of protein 3A and 3B was hydrolysed, whereas no hydrolysis was observed for protein 3C. This was further associated with an approximately 30% decreased expression level of protein 3A and 3B relative to 3C.

2.3. Expression of CT-intein Fusion Proteins

The protein 4 family comprising 4A, 4B, and 4C include hCT fused between an amino-terminal extension (containing a His tag (SEQ ID NO: 5) and an enterokinase protease site (SEQ ID NO: 9)) and a carboxy-terminal Mxe GyrA intein variant being native Mxe GyrA, [106(GS)$_4$161]-Mxe GyrA, and [Cys3, 106(GS)$_4$161]-Mxe GyrA, respectively. All three proteins were obtained mainly in the soluble fraction without any hydrolysis (Table 4). In this case the expression levels of proteins 4A and 4B were higher compared to protein 4C.

2.4. Expression of PP-intein Fusion Proteins

The protein 5 family comprising 5A, 5B, and 5C include hPP fused between an amino-terminal extension (containing a His tag (SEQ ID NO: 5) and an enterokinase protease site (SEQ ID NO: 9)) and a carboxy-terminal Mxe GyrA intein variant being native Mxe GyrA, [106(GS)$_4$161]-Mxe GyrA, and [Cys3, 106(GS)$_4$161]-Mxe GyrA, respectively. Proteins 5A-5C were obtained in the soluble fraction (Table 4). Whereas approximately 50% hydrolysis was observed for protein 5A and 5B, no hydrolysis was observed for protein 5C. This was associated with approximately 10-20% increased expression level of protein 5C compared to 5A and 5B.

2.5. Expression of Amylin-intein Fusion Proteins

The protein 7 family comprising 7A, 7B, and 7C include [Asp14, Arg17, Pro21, Pro27, Arg35]-hAmylin fused between an amino-terminal histidine rich tridecapeptide extension that can be removed by alp protease (SEQ ID NO: 7) and a carboxy-terminal Mxe GyrA intein variant being native Mxe GyrA, [106(GS)$_4$161]-Mxe GyrA, and [Cys3, 106(GS)$_4$161]-Mxe GyrA, respectively. Whereas proteins 7A and 7B were both mainly obtained in the soluble fraction, protein 7C was obtained as a mixture of soluble and insoluble protein (Table 4). For both protein 7A and protein 7B extensive hydrolysis was observed, whereas the engineered intein of protein 7C was associated with no hydrolysis. This resulted in an increased expression level by 7-13% of protein 7C compared to 7A and 7B.

In conclusion, the [Cys3, 106(GS)$_4$161]-Mxe GyrA intein (SEQ ID NO: 20) generally resulted in decreased hydrolysis and a concomitant increase in the expression level of fusion proteins compared to the wildtype Mxe GyrA (SEQ ID NO: 17) and minimized [106(GS)$_4$161]-Mxe GyrA (SEQ ID NO: 19) inteins.

TABLE 4

Hydrolysis levels, expression levels and solubility of fusion proteins of the native Mxe GyrA, [106(GS)$_4$161]-Mxe GyrA, and [Cys3, 106(GS)$_4$161]-Mxe GyrA inteins.

| No. | Induced sample Protein (area) | Induced sample Intein (area) | Hydrolysis [%]$^a$ | Expression level [%]$^b$ | Soluble protein (area)$^c$ | Insoluble protein (area)$^c$ | Soluble protein [%]$^d$ |
|---|---|---|---|---|---|---|---|
| 1A | 13381 | 12560 | 48 | 71 | 13290 | 537 | 96 |
| 1B | 12120 | 9299 | 43 | 64 | 10070 | 459 | 96 |
| 1C | 18726 | 0 | 0 | 100 | 10277 | 4344 | 70 |
| 2A | 9067 | 13958 | 61 | 58 | 11110 | 441 | 96 |
| 2B | 10199 | 9631 | 49 | 73 | 10721 | 1361 | 89 |
| 2C | 13892 | 0 | 0 | 100 | 9211 | 1381 | 87 |
| 3A | 15504 | 18586 | 55 | 73 | 29018 | 777 | 97 |
| 3B | 15516 | 14075 | 48 | 73 | 18273 | 1477 | 93 |
| 3C | 21352 | 0 | 0 | 100 | 15325 | 2242 | 87 |
| 4A | 15028 | 0 | 0 | 120 | 5492 | 809 | 87 |
| 4B | 13137 | 0 | 0 | 105 | 6787 | 1736 | 80 |
| 4C | 12523 | 0 | 0 | 100 | 6540 | 924 | 88 |
| 5A | 13353 | 8285 | 38 | 80 | 8322 | 972 | 90 |
| 5B | 15544 | 10519 | 40 | 93 | 17907 | 1719 | 91 |
| 5C | 16778 | 0 | 0 | 100 | 11792 | 1241 | 90 |
| 6A | 14438 | 16435 | 53 | 85 | 23601 | 761 | 97 |
| 6B | 11385 | 9574 | 46 | 67 | 15269 | 895 | 94 |
| 6C | 16938 | 0 | 0 | 100 | 8951 | 3202 | 74 |
| 7A | 18941 | 25732 | 58 | 87 | 38419 | 2092 | 95 |
| 7B | 19832 | 13501 | 41 | 91 | 12629 | 5249 | 71 |
| 7C | 21811 | 0 | 0 | 100 | 6073 | 8547 | 42 |

$^a$Estimated as area$_{intein}$/(area$_{protein}$ + area$_{intein}$)
$^b$Expression levels of fusion proteins C was set to 100% and that of fusion proteins A and B were calculated relative to C.
$^c$Sum of areas of intein and fusion protein.
$^d$Estimated as area$_{soluble\ protein}$/(area$_{soluble\ protein}$ + area$_{insoluble\ protein}$).

Example 3

Peptide α-thioester Formation Using Engineered Inteins

To examine the effect of the engineered [Cys3, 106(GS)$_4$161]-Mxe GyrA intein on the yield of the target peptide the amino terminal tagged [Gly4]-hPYY(4-36) α-thioester was isolated from fusion protein 1A, 1C, and 1D containing native Mxe GyrA (SEQ ID NO: 17), [Cys3, 106(GS)$_4$161]-Mxe GyrA (SEQ ID NO: 20), and [Cys3]-Mxe GyrA (SEQ ID NO: 18) respectively.

The fusion proteins 1A, 1C and 1D were expressed in shake-flasks containing 200 mL LB medium as described in the general methods. SDS-PAGE analysis was performed as described in the general methods and showed that >90% of the fusion proteins were in the insoluble fraction. The harvested cells were lysed in 25 mM sodium phosphate pH 5 buffer by sonication and the insoluble fraction was washed twice in wash buffer [25 mM sodium phosphate, 1 mM EDTA, 1% Triton X-100, pH 7] followed by one wash in 100 mM sodium phosphate pH 7.5 buffer. The isolated inclusion bodies were re-suspended in solubilization buffer [100 mM sodium phosphate, 8 M urea, 1 mM TCEP, 1 mM EDTA, pH 7.5] (20 mL) and incubated for 2 h at 5° C. with weak agitation. The expression yield was estimated by RP-UPLC method A. The sample was filtered (0.45 μm) and refolded by rapid dilution into 9 volumes of cold refolding buffer [100 mM sodium phosphate, 1.3 M urea, 150 mM NaCl, 1 mM EDTA, 1 mM TCEP, pH 7.5] resulting in a concentration of 135 mM NaCl and 2 M urea. Immediately after dilution, the cleavage was initiated by adding MESNa to a final concentration of 100 mM. Reactions were allowed at 5° C. for 20 h at pH 7.3. The thiol-induced cleavages were monitored by RP-UPLC method B and LC-MS method A. The observed masses of fusion proteins and their corresponding inteins correlated with the expected (Table 3).

The thiol-induced reaction mixtures were diluted by three volumes of buffer A [50 mM sodium phosphate, 1 mM EDTA, pH 7] to decrease the conductivity to approximately 12 mS/cm before loading onto a HiTrap SP Sepharose HP (16×25 mm, 5 mL, GE Healthcare) column at 5 mL/min using an AKTA explorer 100 system (GE Healthcare). The column was washed with 9 column volumes of buffer A and the amino-terminal tagged [Gly4]-hPYY(4-36) α-thioester was eluted using a linear gradient of 0-100% buffer A containing 1 M NaCl over 20 column volumes at 3 mL/min. Fractions containing the α-thioester were pooled and the amount was estimated by RP-UPLC method C. The identity of the product was confirmed by ESI-MS resulting in a deconvoluted mass of 12315.35 Da (expected: 12315.09). The yields are listed in Table 5.

TABLE 5

Purification of N-tagged [Gly4]-hPYY(4-36) α-thioester using different intein variants[a].

| Protein | Yield of fusion protein (mg/L) | Yield of α-thioester[b] (mg/L) | α-acid impurity[c] (%) |
|---|---|---|---|
| 1A | 119 | 23 | 6.0 |
| 1C | 147 | 43 | 1.5 |
| 1D | 130 | 24 | 1.5 |

[a]The yields obtained from 200 mL shake flask cultures were normalized to yield per liter culture. Data are presented as means from two independent experiments.
[b]Amount of α-acid by-product not included.
[c]Estimated as area$_{\alpha\text{-acid}}$/(area$_{\alpha\text{-acid}}$ + area$_{\alpha\text{-thioester}}$) by rp-UPLC.

In conclusion, the yield of amino-terminal tagged [Gly4]-hPYY(4-36) α-thioester obtained from protein 1A containing the wild-type Mxe GyrA intein (SEQ ID NO: 14) was similar to that of protein 1D containing the [Cys3]-Mxe GyrA (SEQ ID NO: 18), which indicated that the T3C mutation itself did not increase the amount of target peptide (Table 5). However, when isolated from protein 1C containing the [Cys3, 106(GS)4161]-Mxe GyrA intein (SEQ ID NO: 20), the yield was increased by approximately 80% compared to protein 1A, indicating that the engineered intein comprising a minimized size and a T3C mutation positively affected the target peptide yield. Importantly, the amount of amino-terminal tagged [Gly4]-hPYY(4-36) α-acid by-product was reduced for protein 1C and 1D compared to 1A, indicating that the T3C mutation also have a beneficial effect during purification.

The [Cys3, 106(GS)4161]-Mxe GyrA intein (SEQ ID NO: 20) intein increases the expression level of the fusion protein and enhances the yield of the target peptide. As this was not observed for the [Cys3]-Mxe GyrA intein (SEQ ID NO: 18), the minimized size contributes to these enhanced properties.

Example 4

Generation of an α-amidated Peptide Using the [Cys3, 106(GS)4161]-Mxe GyrA Intein The potential usage of fusion proteins comprising the engineered intein for large scale production of α-amidated peptides depends on its ability to express under high-cell density conditions. This was demonstrated for [Gly4]-hPYY (4-36)-NH$_2$, which was isolated from protein 1C after fed-batch fermentation in a bio-reactor.

4.1. Fed-Batch Fermentation of Fusion Protein 1C

A pre-culture of BL21(DE3) cells containing plasmid p1C was grown in LB medium supplied with 100 µg/mL ampicillin in a shaker flask for 6-8 h. Fermentations were carried out under aerobic conditions in 500 mL bioreactors (DasGib Technology) with an initial volume of 200 mL of a defined fermentation medium with glucose and ammonia as carbon and nitrogen sources, respectively, and with 100 µg/mL ampicillin added after sterilisation (autoclavation at 121° C. for 30 min). The pre-culture was inoculated into a bioreactor to reach an initial OD$_{600}$ of about 0.2. The pH was maintained at 7.0 by addition of 5 N NH$_4$OH, the temperature was maintained at 37° C. and an air flow rate of 0.4 L/min was sparkled through the culture broth throughout the fermentation period. The agitation speed (400-1200 rpm) was controlled to reach a dissolved oxygen level of at least 30% O$_2$ saturation. The initial glucose concentration in the fermentation medium was 10 g/L and from 5 h of fermentation a glucose feed supplied with magnesium and trace metals was added continuously in increasing steps until a final feed rate of 10 g glucose/L/h, which was kept until the fermentation stopped. The production of the fusion proteins were induced by the addition of 0.5 mM IPTG at an OD$_{600}$ of 50-60. The fermentation was stopped after 4 h induction. The cells were harvested by centrifugation in a Sorvall RC 6 Plus centrifuge with a F10-6x500y Rotor (13000×g) and stored at −20° C. The cells were re-suspended in lysis buffer [25 mM sodium phosphate, pH 5] to OD$_{600}$ of 40-50 and stirred 1 h at 4° C. Cells were lysed on a constant cell disruption system E615 at a pressure of 1.36 Kbar. The lysed cells were spun down and the supernatant decanted. The insoluble inclusion bodies were washed in wash buffer [25 mM sodium phosphate, pH 7, 5 mM EDTA, 1% Triton X-100] and stirred at 5° C. for 2 h, followed by one wash in MilliQ water. The inclusion bodies were divided equally into 20 smaller fractions.

4.2. Isolation of [Gly4]-hPYY(4-36)-Amide ([Gly4]-hPYY (4-36)-NH$_2$)

Figure 2:
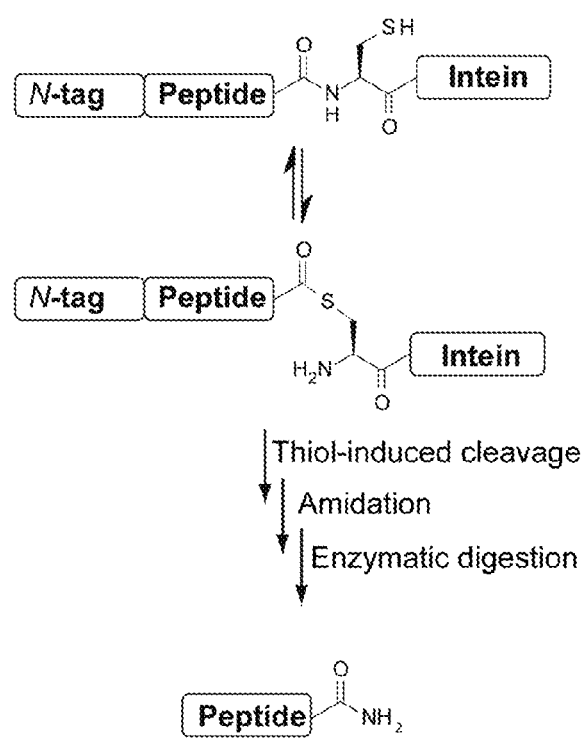
FIG. 2: Schematic representation of the basic principal of making carboxy-terminal modified target peptides. The target peptide is fused to a carboxy-terminal intein that can be liberated by nucleophilic cleavage generating the target peptide as an α-thioester, α-amide or with a synthetic carboxy-terminal fragment. As shown here, the target peptide is further fused to an amino-terminal affinity tag, which can be removed by enzymatic cleavage. This purification tag could also be placed carboxy-terminally to the intein, avoiding the need for processing enzymes.

The strategy is outlined in FIG. 2. Inclusion bodies from 1/20 fed-batch culture were re-suspended in denaturation buffer [25 mM sodium phosphate, 8 M urea, 1 mM TCEP, 1 mM EDTA, pH 7.5] (30 mL) and incubated at 5° C. for 3.5 h with gentle stirring. The yield of fusion protein was estimated by RP-UPLC method A and the sample was diluted to a concentration of approximately 1.2 mg/mL with denaturation buffer. The protein was refolded by adding the protein over 5 min into 8.5 volumes of dilution buffer [25 mM sodium phosphate, 1 mM TCEP, 1 mM EDTA, 0.5 M NaCl, pH 7.5] with stirring. Thiol-induced cleavage was initiated immediately by adding MESNa to 100 mM from a 2 M stock in dilution buffer. Reaction was allowed in the 0.8 M urea and 0.5 M NaCl solution at 5° C. and pH 7.3 overnight with stirring.

Amidation was performed by addition of solid NH$_4$HCO$_3$ to a final concentration of 1 M. The pH of the solution was adjusted to 8.5 with 1 N NaOH and reaction was allowed at 5° C. overnight. Thiol-induced cleavage and amidation reactions were monitored by LC-MS method A (Table 6).

TABLE 6

Masses after thiolysis and amidation of protein 1C.

| amino-terminal tagged | Average masses (Da) | |
|---|---|---|
| [Gly4]-hPYY(4-36) | Expected | Observed |
| α-thioester | 12315.09 | 12315.33 |
| α-amide | 12189.92 | 12189.93 |

The amidation mixture was filtrated (0.22 μm) and the filter washed with 8 M urea. The urea wash was loaded on a Phenomenex Luna column (15 μm and 300 Å; 10×250 mm) followed by the amidation mixture using an AKTA Explorer 100 (GE Healthcare). Amino-terminal tagged [Gly4]-hPYY(4-36)-NH$_2$ was eluted using 0.1% TFA in water (solvent A) and 0.1% TFA in acetonitrile (solvent B) at a linear gradient of 25-45% B. After lyophilization, the protein was dissolved in 25 mM sodium phosphate pH 7.5 buffer and the amino-terminal tag was removed by enzymatic cleavage using HRV14-3C protease that recognizes the sequence EVLFQ/GP specifically. An enzyme to substrate ratio of 1:12 (w/w) was used and incubation was allowed at room temperature for at least 48 h. After adjusting pH of the digest to 4.3, the [Gly4]-hPYY(4-36)-NH$_2$ was recovered by loading at 3 mL/min onto a pre-packed HiTrap SP sepharose HP column (5 mL) equilibrated with eluent A [10 mM NH$_4$HCO$_3$, pH 5.5], followed by a gradient of 0-100% eluent B [10 mM NH$_4$HCO$_3$, pH 8.5] over 5 column volumes and [Gly4]-hPYY(4-36)-NH$_2$ was eluted using isocratic eluent B for 10 CV. Purity and identity of [Gly4]-hPYY(4-36)-NH$_2$ was determined by RP-UPLC method C and characterized by LC-MS method B, whereas yield was estimated by chemoluminescence nitrogen detection (Table 7).

The [Gly4]-hPYY(4-36)-NH$_2$ was isolated in a purity of 99% and yield of 184 mg/L (Table 7).

In conclusion, fusion protein 1C containing the [Cys3, 106(GS)$_4$161]-Mxe GyrA (SEQ ID NO: 20) was successfully expressed under high-cell density conditions and converted into [Gly4]-hPYY(4-36)-NH$_2$, demonstrating the applicability of the engineered intein for production of α-amidated peptides in large-scale.

TABLE 7

Production of α-amidated [Gly4]-hPYY(4-36)-NH$_2$ from fed-batch culture of fusion protein 1C containing the engineered intein[a]

| Protein yield [g/L] | [Gly4]-hPYY(4-36)-NH$_2$ yield [mg/L] | Recovery [mol %] | Purity [%] | Monoisotopic mass of [M + 5H]$^{5+}$ ion | |
|---|---|---|---|---|---|
| | | | | Expected | Observed |
| 4.4 | 184 | 31 | 99 | 773.59 | 773.60 |

[a]The yields obtained from 1/20 of the 200 mL fed-batch cultures were normalized to yield per liter culture. Data are presented as means from two independent cultivations and subsequent purifications.

While certain features of the invention have been illustrated and described herein, many modifications, substitutions, changes, and equivalents will now occur to those of ordinary skilled in the art. It is, therefore, to be understood that the appended claims are intended to cover all such modifications and changes as fall within the true spirit of the invention.

The invention claimed is:

1. A method for producing a target peptide, which comprises the step of expressing the target peptide as part of a fusion protein, wherein said fusion protein comprises the target peptide and an engineered intein, wherein said intein is minimized in size and carries a cysteine mutation in the position corresponding by alignment to position 3 of Mxe GyrA intein (SEQ ID NO:1); wherein said intein is a Mxe GyrA intein minimized in size by excision of the residues corresponding to residues 107-164 of Mxe GyrA intein (SEQ ID NO:1) or a part of the residues corresponding to residues 107-164 of Mxe GyrA intein (SEQ ID NO:1).

2. A method according to claim 1, wherein the excised residues are replaced by a linker comprising 1 to 10 amino acids.

3. A method according to claim 2, wherein the linker comprises from 6 to 10 amino acids, and wherein at least 6 of the amino acids of the linker are glycine and/or serine.

4. A method according to claim 3, wherein the sequence of said intein is SEQ ID NO: 20.

5. A method according to claim 1, wherein the target peptide is selected from PYY, PP, α-CGRP, CT, and amylin or analogues thereof, and wherein the method further comprises a step to convert the target peptide to the α-amidated form.

6. A method according to claim 1, wherein the fusion protein further comprises a purification tag and optionally a protease site, which allows for identification and/or purification by affinity chromatography or other chromatographic methods, and where said protease site allows for detachment of such purification tag.

7. A method according to claim 1, further comprising thiol-induced cleavage of the fusion protein resulting in the α-thioester of the target peptide.

8. A method for producing an α-amidated target peptide, which comprises the step of expressing the target peptide as part of a fusion protein, wherein said fusion protein comprises the target peptide and an intein of SEQ ID NO: 20, and the step of converting the target peptide to the α-amidated form.

9. A method according to claim 1, wherein the fusion protein is expressed in bacteria, yeast, mammalian cells or in a body fluid of a transgenic mammal.

10. A fusion protein comprising a target peptide and an intein, wherein said intein is minimized in size and carries a cysteine mutation in the position corresponding by alignment to position 3 of Mxe GyrA intein (SEQ ID NO:1);
wherein said intein is a Mxe GyrA intein minimized in size by excision of the residues corresponding to residues 107-164 of Mxe GyrA intein (SEQ ID NO:1) or a part of the residues corresponding to residues 107-164 of Mxe GyrA intein (SEQ ID NO:1).

11. An intein which is minimized in size and carries a cysteine mutation in the position corresponding by alignment to position 3 of Mxe GyrA intein (SEQ ID NO:1);
wherein said intein is a Mxe GyrA intein minimized in size by excision of the residues corresponding to residues 107-164 of Mxe GyrA intein (SEQ ID NO:1) or a part of the residues corresponding to residues 107-164 of Mxe GyrA intein (SEQ ID NO:1).

12. An intein according to claim 11, wherein the sequence of said intein is SEQ ID NO: 20.

13. A DNA construct coding for a fusion protein as defined in claim 10.

14. A fusion protein according to claim 10, wherein the excised residues are replaced by a linker comprising 1 to 10 amino acids.

15. An intein according to claim 11, wherein the excised residues are replaced by a linker comprising 1 to 10 amino acids.

* * * * *

SEQUENCE LISTING

```
<160> NUMBER OF SEQ ID NOS: 38

<210> SEQ ID NO 1
<211> LENGTH: 198
<212> TYPE: PRT
<213> ORGANISM: MYCOBACTERIUM XENOPI

<400> SEQUENCE: 1

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Arg Ser Ala Phe Ser Val
            100                 105                 110

Asp Cys Ala Gly Phe Ala Arg Gly Lys Pro Glu Phe Ala Pro Thr Thr
        115                 120                 125

Tyr Thr Val Gly Val Pro Gly Leu Val Arg Phe Leu Glu Ala His His
    130                 135                 140
```

```
Arg Asp Pro Asp Ala Gln Ala Ile Ala Asp Glu Leu Thr Asp Gly Arg
145                 150                 155                 160

Phe Tyr Tyr Ala Lys Val Ala Ser Val Thr Asp Ala Gly Val Gln Pro
                165                 170                 175

Val Tyr Ser Leu Arg Val Asp Thr Ala Asp His Ala Phe Ile Thr Asn
            180                 185                 190

Gly Phe Val Ser His Asn
        195

<210> SEQ ID NO 2
<211> LENGTH: 36
<212> TYPE: PRT
<213> ORGANISM: HOMO SAPIENS

<400> SEQUENCE: 2

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 3
<211> LENGTH: 37
<212> TYPE: PRT
<213> ORGANISM: HOMO SAPIENS

<400> SEQUENCE: 3

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 4
<211> LENGTH: 67
<212> TYPE: PRT
<213> ORGANISM: ARTIFICIAL
<220> FEATURE:
<223> OTHER INFORMATION: tag

<400> SEQUENCE: 4

Met Pro Lys Tyr Leu Gly Val Val Gly Asp Gly Gln Ile Val Lys
1               5                   10                  15

Ala Gly Asn Ile Leu Val Arg Gln Arg Gly Thr Arg Phe Tyr Pro Gly
                20                  25                  30

Lys Asn Val Gly Ile Gly Arg Asp Phe Thr Leu Phe Ala Leu Lys Asp
            35                  40                  45

Gly Arg Val Lys Phe Glu Thr Leu Asn Asn Lys Lys Tyr Val Ser Val
        50                  55                  60

Tyr Glu Glu
65

<210> SEQ ID NO 5
<211> LENGTH: 10
<212> TYPE: PRT
<213> ORGANISM: ARTIFICIAL
<220> FEATURE:
<223> OTHER INFORMATION: tag
```

<400> SEQUENCE: 5

Met Gly Ser Ser His His His His His His
1               5                   10

<210> SEQ ID NO 6
<211> LENGTH: 12
<212> TYPE: PRT
<213> ORGANISM: ARTIFICIAL
<220> FEATURE:
<223> OTHER INFORMATION: tag

<400> SEQUENCE: 6

Met Lys His Gln His Gln His Gln His Gln His Gln
1               5                   10

<210> SEQ ID NO 7
<211> LENGTH: 13
<212> TYPE: PRT
<213> ORGANISM: ARTIFICIAL
<220> FEATURE:
<223> OTHER INFORMATION: tag

<400> SEQUENCE: 7

Met Arg His Gln His Gln His Gln His Gln His Gln Lys
1               5                   10

<210> SEQ ID NO 8
<211> LENGTH: 8
<212> TYPE: PRT
<213> ORGANISM: ARTIFICIAL
<220> FEATURE:
<223> OTHER INFORMATION: protease site

<400> SEQUENCE: 8

Ser Ser Ser Glu Val Leu Phe Gln
1               5

<210> SEQ ID NO 9
<211> LENGTH: 7
<212> TYPE: PRT
<213> ORGANISM: ARTIFICIAL
<220> FEATURE:
<223> OTHER INFORMATION: protease site

<400> SEQUENCE: 9

Ser Ser Asp Asp Asp Asp Lys
1               5

<210> SEQ ID NO 10
<211> LENGTH: 33
<212> TYPE: PRT
<213> ORGANISM: ARTIFICIAL
<220> FEATURE:
<223> OTHER INFORMATION: hPYY variant

<400> SEQUENCE: 10

Gly Pro Glu Ala Pro Gly Glu Asp Ala Ser Pro Glu Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 11
<211> LENGTH: 34

<212> TYPE: PRT
<213> ORGANISM: ARTIFICIAL
<220> FEATURE:
<223> OTHER INFORMATION: hPYY variant

<400> SEQUENCE: 11

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 12
<211> LENGTH: 37
<212> TYPE: PRT
<213> ORGANISM: HOMO SAPIENS

<400> SEQUENCE: 12

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
            35

<210> SEQ ID NO 13
<211> LENGTH: 32
<212> TYPE: PRT
<213> ORGANISM: HOMO SAPIENS

<400> SEQUENCE: 13

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 14
<211> LENGTH: 36
<212> TYPE: PRT
<213> ORGANISM: HOMO SAPIENS

<400> SEQUENCE: 14

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Met Leu Thr
            20                  25                  30

Arg Pro Arg Tyr
            35

<210> SEQ ID NO 15
<211> LENGTH: 34
<212> TYPE: PRT
<213> ORGANISM: ARTIFICIAL
<220> FEATURE:
<223> OTHER INFORMATION: hPYY variant

<400> SEQUENCE: 15

Ile Arg Pro Glu Ala Pro Gly Glu Asp Ala Ser Pro Glu Glu Leu Gln
1               5                   10                  15

```
Arg Tyr Tyr Ala Ser Leu Arg His Tyr Leu Asn Lys Val Thr Arg Gln
            20                  25                  30

Arg Tyr

<210> SEQ ID NO 16
<211> LENGTH: 36
<212> TYPE: PRT
<213> ORGANISM: ARTIFICIAL
<220> FEATURE:
<223> OTHER INFORMATION: hAmylin variant

<400> SEQUENCE: 16

Cys Asn Thr Ala Thr Cys Ala Thr Gln Arg Leu Ala Asp Phe Leu Arg
1               5                   10                  15

His Ser Ser Pro Asn Phe Gly Ala Ile Pro Ser Ser Thr Asn Val Gly
            20                  25                  30

Ser Arg Thr Tyr
        35

<210> SEQ ID NO 17
<211> LENGTH: 198
<212> TYPE: PRT
<213> ORGANISM: ARTIFICIAL
<220> FEATURE:
<223> OTHER INFORMATION: Intein variant

<400> SEQUENCE: 17

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
            35                  40                  45

Arg Leu Phe His Ser Gly Glu His Pro Val Tyr Thr Val Arg Thr Val
        50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Arg Ser Ala Phe Ser Val
            100                 105                 110

Asp Cys Ala Gly Phe Ala Arg Gly Lys Pro Glu Phe Ala Pro Thr Thr
        115                 120                 125

Tyr Thr Val Gly Val Pro Gly Leu Val Arg Phe Leu Glu Ala His His
    130                 135                 140

Arg Asp Pro Asp Ala Gln Ala Ile Ala Asp Glu Leu Thr Asp Gly Arg
145                 150                 155                 160

Phe Tyr Tyr Ala Lys Val Ala Ser Val Thr Asp Ala Gly Val Gln Pro
                165                 170                 175

Val Tyr Ser Leu Arg Val Asp Thr Ala Asp His Ala Phe Ile Thr Asn
            180                 185                 190

Gly Phe Val Ser His Ala
        195

<210> SEQ ID NO 18
<211> LENGTH: 198
<212> TYPE: PRT
<213> ORGANISM: ARTIFICIAL
```

<220> FEATURE:
<223> OTHER INFORMATION: Intein variant

<400> SEQUENCE: 18

Cys Ile Cys Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Arg Ser Ala Phe Ser Val
            100                 105                 110

Asp Cys Ala Gly Phe Ala Arg Gly Lys Pro Glu Phe Ala Pro Thr Thr
        115                 120                 125

Tyr Thr Val Gly Val Pro Gly Leu Val Arg Phe Leu Glu Ala His His
    130                 135                 140

Arg Asp Pro Asp Ala Gln Ala Ile Ala Asp Glu Leu Thr Asp Gly Arg
145                 150                 155                 160

Phe Tyr Tyr Ala Lys Val Ala Ser Val Thr Asp Ala Gly Val Gln Pro
                165                 170                 175

Val Tyr Ser Leu Arg Val Asp Thr Ala Asp His Ala Phe Ile Thr Asn
            180                 185                 190

Gly Phe Val Ser His Ala
            195

<210> SEQ ID NO 19
<211> LENGTH: 152
<212> TYPE: PRT
<213> ORGANISM: ARTIFICIAL
<220> FEATURE:
<223> OTHER INFORMATION: Intein variant

<400> SEQUENCE: 19

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Gly Ser Gly Ser Gly Ser
            100                 105                 110

Gly Ser Phe Tyr Tyr Ala Lys Val Ala Ser Val Thr Asp Ala Gly Val
        115                 120                 125

Gln Pro Val Tyr Ser Leu Arg Val Asp Thr Ala Asp His Ala Phe Ile

```
                    130                 135                 140

Thr Asn Gly Phe Val Ser His Ala
145                 150

<210> SEQ ID NO 20
<211> LENGTH: 152
<212> TYPE: PRT
<213> ORGANISM: ARTIFICIAL
<220> FEATURE:
<223> OTHER INFORMATION: Intein variant

<400> SEQUENCE: 20

Cys Ile Cys Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Gly Ser Gly Ser Gly Ser
            100                 105                 110

Gly Ser Phe Tyr Tyr Ala Lys Val Ala Ser Val Thr Asp Ala Gly Val
        115                 120                 125

Gln Pro Val Tyr Ser Leu Arg Val Asp Thr Ala Asp His Ala Phe Ile
    130                 135                 140

Thr Asn Gly Phe Val Ser His Ala
145                 150

<210> SEQ ID NO 21
<211> LENGTH: 152
<212> TYPE: PRT
<213> ORGANISM: ARTIFICIAL
<220> FEATURE:
<223> OTHER INFORMATION: Intein variant

<400> SEQUENCE: 21

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Arg Ser Ala Phe Ser Asp
            100                 105                 110

Gly Arg Phe Tyr Tyr Ala Lys Val Ala Ser Val Thr Asp Ala Gly Val
        115                 120                 125
```

-continued

Gln Pro Val Tyr Ser Leu Arg Val Asp Thr Ala Asp His Ala Phe Ile
            130                 135                 140

Thr Asn Gly Phe Val Ser His Ala
145                 150

<210> SEQ ID NO 22
<211> LENGTH: 144
<212> TYPE: PRT
<213> ORGANISM: ARTIFICIAL
<220> FEATURE:
<223> OTHER INFORMATION: Intein variant

<400> SEQUENCE: 22

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
                20                  25                  30

Ile Asp Leu Lys Val Leu Asp Arg His Gly Asn Pro Val Leu Ala Asp
            35                  40                  45

Arg Leu Phe His Ser Gly Glu His Pro Val Tyr Thr Val Arg Thr Val
        50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Phe Tyr Tyr Ala Lys Val
            100                 105                 110

Ala Ser Val Thr Asp Ala Gly Val Gln Pro Val Tyr Ser Leu Arg Val
        115                 120                 125

Asp Thr Ala Asp His Ala Phe Ile Thr Asn Gly Phe Val Ser His Ala
    130                 135                 140

<210> SEQ ID NO 23
<211> LENGTH: 158
<212> TYPE: PRT
<213> ORGANISM: ARTIFICIAL
<220> FEATURE:
<223> OTHER INFORMATION: Intein variant

<400> SEQUENCE: 23

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
                20                  25                  30

Ile Asp Leu Lys Val Leu Asp Arg His Gly Asn Pro Val Leu Ala Asp
            35                  40                  45

Arg Leu Phe His Ser Gly Glu His Pro Val Tyr Thr Val Arg Thr Val
        50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Arg Ser Ala Phe Ser Leu
            100                 105                 110

Asp Arg His Gly Asn Asp Gly Arg Phe Tyr Tyr Ala Lys Val Ala Ser
        115                 120                 125

Val Thr Asp Ala Gly Val Gln Pro Val Tyr Ser Leu Arg Val Asp Thr
    130                 135                 140

```
Ala Asp His Ala Phe Ile Thr Asn Gly Phe Val Ser His Ala
145                 150                 155
```

<210> SEQ ID NO 24
<211> LENGTH: 150
<212> TYPE: PRT
<213> ORGANISM: ARTIFICIAL
<220> FEATURE:
<223> OTHER INFORMATION: Intein variant

<400> SEQUENCE: 24

```
Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Leu Asp Arg His Gln Asn
            100                 105                 110

Phe Tyr Tyr Ala Lys Val Ala Ser Val Thr Asp Ala Gly Val Gln Pro
        115                 120                 125

Val Tyr Ser Leu Arg Val Asp Thr Ala Asp His Ala Phe Ile Thr Asn
    130                 135                 140

Gly Phe Val Ser His Ala
145             150
```

<210> SEQ ID NO 25
<211> LENGTH: 151
<212> TYPE: PRT
<213> ORGANISM: ARTIFICIAL
<220> FEATURE:
<223> OTHER INFORMATION: Intein variant

<400> SEQUENCE: 25

```
Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Arg Asp Val Glu Thr Gly
            100                 105                 110

Glu Phe Tyr Tyr Ala Lys Val Ala Ser Val Thr Asp Ala Gly Val Gln
        115                 120                 125

Pro Val Tyr Ser Leu Arg Val Asp Thr Ala Asp His Ala Phe Ile Thr
```

Asn Gly Phe Val Ser His Ala
145                 150

<210> SEQ ID NO 26
<211> LENGTH: 151
<212> TYPE: PRT
<213> ORGANISM: ARTIFICIAL
<220> FEATURE:
<223> OTHER INFORMATION: Intein variant

<400> SEQUENCE: 26

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
                20                  25                  30

Ile Asp Leu Lys Val Leu Asp Arg His Gly Asn Pro Val Leu Ala Asp
            35                  40                  45

Arg Leu Phe His Ser Gly Glu His Pro Val Tyr Thr Val Arg Thr Val
        50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Ala Asp Asn Leu Ala Leu
            100                 105                 110

Ala Phe Tyr Tyr Ala Lys Val Ala Ser Val Thr Asp Ala Gly Val Gln
        115                 120                 125

Pro Val Tyr Ser Leu Arg Val Asp Thr Ala Asp His Ala Phe Ile Thr
    130                 135                 140

Asn Gly Phe Val Ser His Ala
145                 150

<210> SEQ ID NO 27
<211> LENGTH: 152
<212> TYPE: PRT
<213> ORGANISM: ARTIFICIAL
<220> FEATURE:
<223> OTHER INFORMATION: Intein variant

<400> SEQUENCE: 27

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
                20                  25                  30

Ile Asp Leu Lys Val Leu Asp Arg His Gly Asn Pro Val Leu Ala Asp
            35                  40                  45

Arg Leu Phe His Ser Gly Glu His Pro Val Tyr Thr Val Arg Thr Val
        50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Gly Arg Gly Ser Gly Arg
            100                 105                 110

Gly Ser Phe Tyr Tyr Ala Lys Val Ala Ser Val Thr Asp Ala Gly Val
        115                 120                 125

Gln Pro Val Tyr Ser Leu Arg Val Asp Thr Ala Asp His Ala Phe Ile
            130                 135                 140

Thr Asn Gly Phe Val Ser His Ala
145                 150

<210> SEQ ID NO 28
<211> LENGTH: 151
<212> TYPE: PRT
<213> ORGANISM: ARTIFICIAL
<220> FEATURE:
<223> OTHER INFORMATION: Intein variant

<400> SEQUENCE: 28

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gly Ser Gly Ser Gly Ser Gly
            100                 105                 110

Ser Phe Tyr Tyr Ala Lys Val Ala Ser Val Thr Asp Ala Gly Val Gln
        115                 120                 125

Pro Val Tyr Ser Leu Arg Val Asp Thr Ala Asp His Ala Phe Ile Thr
    130                 135                 140

Asn Gly Phe Val Ser His Ala
145                 150

<210> SEQ ID NO 29
<211> LENGTH: 150
<212> TYPE: PRT
<213> ORGANISM: ARTIFICIAL
<220> FEATURE:
<223> OTHER INFORMATION: Intein variant

<400> SEQUENCE: 29

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Gly Ser Gly Ser Gly Ser Gly Ser
            100                 105                 110

Phe Tyr Tyr Ala Lys Val Ala Ser Val Thr Asp Ala Gly Val Gln Pro
        115                 120                 125

```
Val Tyr Ser Leu Arg Val Asp Thr Ala Asp His Ala Phe Ile Thr Asn
        130                 135                 140

Gly Phe Val Ser His Ala
145                 150

<210> SEQ ID NO 30
<211> LENGTH: 149
<212> TYPE: PRT
<213> ORGANISM: ARTIFICIAL
<220> FEATURE:
<223> OTHER INFORMATION: Intein variant

<400> SEQUENCE: 30

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Gly Ser Gly Ser Gly Ser Gly Ser Phe
            100                 105                 110

Tyr Tyr Ala Lys Val Ala Ser Val Thr Asp Ala Gly Val Gln Pro Val
        115                 120                 125

Tyr Ser Leu Arg Val Asp Thr Ala Asp His Ala Phe Ile Thr Asn Gly
    130                 135                 140

Phe Val Ser His Ala
145

<210> SEQ ID NO 31
<211> LENGTH: 151
<212> TYPE: PRT
<213> ORGANISM: ARTIFICIAL
<220> FEATURE:
<223> OTHER INFORMATION: Intein variant

<400> SEQUENCE: 31

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Gly Ser Gly Ser Gly Ser
            100                 105                 110

Gly Ser Tyr Tyr Ala Lys Val Ala Ser Val Thr Asp Ala Gly Val Gln
```

```
                    115                 120                 125
Pro Val Tyr Ser Leu Arg Val Asp Thr Ala Asp His Ala Phe Ile Thr
    130                 135                 140
Asn Gly Phe Val Ser His Ala
145                 150

<210> SEQ ID NO 32
<211> LENGTH: 150
<212> TYPE: PRT
<213> ORGANISM: ARTIFICIAL
<220> FEATURE:
<223> OTHER INFORMATION: Intein variant

<400> SEQUENCE: 32

Cys Ile Thr Gly Asp Ala Leu Val Ala Leu Pro Glu Gly Glu Ser Val
1               5                   10                  15
Arg Ile Ala Asp Ile Val Pro Gly Ala Arg Pro Asn Ser Asp Asn Ala
            20                  25                  30
Ile Asp Leu Lys Val Leu Asp Arg His Gly Asn Pro Val Leu Ala Asp
        35                  40                  45
Arg Leu Phe His Ser Gly Glu His Pro Val Tyr Thr Val Arg Thr Val
    50                  55                  60
Glu Gly Leu Arg Val Thr Gly Thr Ala Asn His Pro Leu Leu Cys Leu
65                  70                  75                  80
Val Asp Val Ala Gly Val Pro Thr Leu Leu Trp Lys Leu Ile Asp Glu
                85                  90                  95
Ile Lys Pro Gly Asp Tyr Ala Val Ile Gln Gly Ser Gly Ser Gly Ser
            100                 105                 110
Gly Ser Tyr Ala Lys Val Ala Ser Val Thr Asp Ala Gly Val Gln Pro
        115                 120                 125
Val Tyr Ser Leu Arg Val Asp Thr Ala Asp His Ala Phe Ile Thr Asn
    130                 135                 140
Gly Phe Val Ser His Ala
145                 150

<210> SEQ ID NO 33
<211> LENGTH: 149
<212> TYPE: PRT
<213> ORGANISM: ARTIFICIAL
<220> FEATURE:
<223> OTHER INFORMATION: Intein variant

<400> SEQUENCE: 33

Cys Ile Thr Gly Asp Ala Leu Val Ala Leu Pro Glu Gly Glu Ser Val
1               5                   10                  15
Arg Ile Ala Asp Ile Val Pro Gly Ala Arg Pro Asn Ser Asp Asn Ala
            20                  25                  30
Ile Asp Leu Lys Val Leu Asp Arg His Gly Asn Pro Val Leu Ala Asp
        35                  40                  45
Arg Leu Phe His Ser Gly Glu His Pro Val Tyr Thr Val Arg Thr Val
    50                  55                  60
Glu Gly Leu Arg Val Thr Gly Thr Ala Asn His Pro Leu Leu Cys Leu
65                  70                  75                  80
Val Asp Val Ala Gly Val Pro Thr Leu Leu Trp Lys Leu Ile Asp Glu
                85                  90                  95
Ile Lys Pro Gly Asp Tyr Ala Val Ile Gln Gly Ser Gly Ser Gly Ser
            100                 105                 110
```

Gly Ser Ala Lys Val Ala Ser Val Thr Asp Ala Gly Val Gln Pro Val
            115                 120                 125
Tyr Ser Leu Arg Val Asp Thr Ala Asp His Ala Phe Ile Thr Asn Gly
        130                 135                 140
Phe Val Ser His Ala
145

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Gly Ser Gly Ser Gly Ser Gly Ser
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic

<400> SEQUENCE: 35

Leu Asp Arg His Gly Asn
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic

<400> SEQUENCE: 36

Ala Asp Asn Leu Ala Leu Ala
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic

<400> SEQUENCE: 37

Arg Asp Val Glu Thr Gly Glu
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Gly Arg Gly Ser Gly Arg Gly Ser
1               5